US007785776B2

(12) United States Patent
Wittwer et al.

(10) Patent No.: US 7,785,776 B2
(45) Date of Patent: Aug. 31, 2010

(54) GENOTYPING BY AMPLICON MELTING CURVE ANALYSIS

(75) Inventors: Carl T. Wittwer, Salt Lake City, UT (US); Cameron Gundry, Cottonwood Heights, UT (US); Richard David Abbott, Draper, UT (US); Derek Allen David, Tooele, UT (US)

(73) Assignees: Idaho Technology, Inc., Salt Lake City, UT (US); University of Utah Research Foundation, Salt Lake City, UT (US)

( * ) Notice: Subject to any disclaimer, the term of this patent is extended or adjusted under 35 U.S.C. 154(b) by 920 days.

(21) Appl. No.: 10/431,804

(22) Filed: May 8, 2003

(65) Prior Publication Data

US 2003/0224434 A1 Dec. 4, 2003

Related U.S. Application Data

(60) Provisional application No. 60/380,354, filed on May 13, 2002, provisional application No. 60/386,975, filed on Jun. 7, 2002.

(51) Int. Cl.
*C12Q 1/68* (2006.01)
*C12P 19/34* (2006.01)
(52) U.S. Cl. .......................................... 435/6; 435/91.2
(58) Field of Classification Search ........................ None
See application file for complete search history.

(56) References Cited

U.S. PATENT DOCUMENTS

| | | | | |
|---|---|---|---|---|
| 5,327,254 | A | * | 7/1994 | Daher .......................... 382/298 |
| 5,403,707 | A | | 4/1995 | Atwood et al. |
| 5,475,098 | A | | 12/1995 | Hall et al. |
| 5,591,578 | A | | 1/1997 | Meade et al. |
| 5,888,739 | A | | 3/1999 | Pitner et al. |
| 6,106,777 | A | | 8/2000 | Fujita et al. |
| 6,140,054 | A | | 10/2000 | Wittwer et al. |
| 6,174,670 | B1 | | 1/2001 | Wittwer |
| 6,197,520 | B1 | * | 3/2001 | Wittwer et al. ................. 435/6 |
| 6,346,386 | B1 | | 2/2002 | Elenitoba-Johnson |
| 6,492,121 | B2 | * | 12/2002 | Kurane et al. .................. 435/6 |
| 6,566,141 | B2 | | 5/2003 | Fujiwake et al. |
| 6,635,427 | B2 | * | 10/2003 | Wittwer et al. ................. 435/6 |
| 6,642,000 | B1 | * | 11/2003 | Strizhkov et al. .............. 435/6 |
| 2001/0000175 | A1 | | 4/2001 | Kurane et al. |
| 2003/0165859 | A1 | * | 9/2003 | Nazarenko et al. ............. 435/6 |
| 2006/0019253 | A1 | * | 1/2006 | Wittwer et al. ................. 435/6 |

FOREIGN PATENT DOCUMENTS

| | | |
|---|---|---|
| EP | 1 195 443 A2 | 4/2002 |
| WO | WO93/16194 | 8/1993 |
| WO | WO97/46707 | 12/1997 |
| WO | WO97/46712 | 12/1997 |
| WO | WO97/46714 | 12/1997 |

OTHER PUBLICATIONS

Crockett et al. "Fluorescein labeled oligonucleotides for Real-Time PCR using the inherent quenching of deoxyguanosine nucleotides" Analytical Biochemistry, 2001, vol. 200, p. 89-97.*
Wittwer et al. "Real-Time Multiplex PCR assays" Methods, 2001, vol. 25, p. 430-442.*
Nuovo et al. (Journal of Histochemistry & Cytometry 1999, vol. 47, No. 3, p. 273-279).*
Germer and Higuchi (Genome Research, 1999, vol. 9, p. 72-78).*
Ricevuto et al. (Clinical Cancer Research, 2001, vol. 7, p. 1638-1646).*
Savage et al. (Tissue Antigens 1996, vol. 47, No. 4, p. 284-292).*
Ririe et al. (Analytical Biochemistry, 1997, vol. 245, p. 154-160).*
Elenitoba-Johnson et al. (American Journal of Pathology, 2001, vol. 150, No. 3, p. 845-853).*
Gonzalgo et al. (Nucleic Acids Research, 1997, vol. 25, No. 12, p. 2529-2531).*
Wittwer et al. (Biotechniques, 1997, vol. 22, No. 1, p. 176-181).*
Szuhai et al. (Amer. J. Path., 2001, vol. 159, No. 5, p. 1651-1660).*
Schalasta et al. (Infection, 2000, vol. 28, No. 2, p. 85-91).*
Aoshima et al. (Clinical Chemistry, 2000, vol. 46, No. 1, p. 119-122).*
Crockett et al. (Analytical Biochemistry, 2001, vol. 290, p. 89-97).*
Wittwer et al. (Methods, 2001, vol. 25, p. 430-442).*
Steger et al. (Nucleic Acids Research, 1987, 15(13):5085-5106).*
"Color Multiplexing Hybridization Probes Using the Apolipoprotein E Locus AS A Model System For Genotyping," Philip S. Bernard et al., *Analytical Biochemistry*, 273, 221-228 (1999).
"Universal Primer Quantitative Fluorescent multiplex (UPQFM) PCR: A Method To Detect Major And Minor Rearrangements Of the Low Density Lipoprotein Receptor Gene," Karen E. Heath et al., *J. Med. Genet.*, 2000; 37:272-280.
HyBeacon Probes: A New Tool For DNA Sequence Detection And Allele Discrimination, D.J. French et al., *Molecular and Cellular Probes*, 15, 363-374 (2001).
"Fluorescence-Quenching Phenonmenon by Photoinduced Electron Transfer Between A Fluorescent Dye and a Nucleotide Base," Masaki Torimura et al., *Analytical Sciences*, Jan. 2001, vol. 17, 155-160.
"Fluorescein-Labeled Oligonucleotides for Real-Time PCR: Using the Inherent Quenching of Deoxyguanosine Nucleotides," Andrew O. Crockett et al., *Analytical Biochemistry*, 290, 89-97 (2001).
"Fluorescence Quenching: A Tool for Single-Molecule Protein-Folding Study," Xiaowei Zhuang et al., *PNAS*, Dec. 19, 2000, vol. 97, No. 26, 14241-14244.
Elenitoba-Johnson KS, Bohling SD.,"Solution-based scanning for single-base alterations using a double-stranded DNA binding dye and fluorescence-melting profiles". *Am J Pathol.* Sep. 2001;159(3):845-53.

(Continued)

*Primary Examiner*—Gary Benzion
*Assistant Examiner*—Stephanie K Mummert
(74) *Attorney, Agent, or Firm*—Barnes & Thornburg LLP

(57) ABSTRACT

Methods for analyzing a target nucleic acid are provided. A fluorescent label attached to a nucleic acid is incorporated into at least one strand of the target nucleic acid and the methods include monitoring change in fluorescence emission resulting from dissociation of the labeled strand of the amplification product from its complementary strand.

19 Claims, 22 Drawing Sheets

OTHER PUBLICATIONS

Orita, O., et al., Proc. Natl. Acad. Sci. USA. 86:2766-2770, 1989.
Nataraj, A.J., et al., Electrophoresis. 20:1177-1185, 1999.
Abrams, E.S., et al., Genomics 7:463-475, 1990.
Wartell, R.M., et al., J. Chromatogr. A. 806:169-185, 1998.
Hawkins G.A., et al., Electrophoresis, 20:1171-1176, 1999.
Narayanaswami, G., et al., Genetic Testing. 5:9-16, 2001.
Wittwer C.T., et al., BioTechniques, 22:130-138, 1997.
Ririe K.M., et al., Anal. Biochem, 245:154-160, 1997.
Lipsky, R.H., et al., Clin. Chem. 47:635-644, 2001.
Wittwer C.T., et al., Methods, 25:430-442, 2001.
Whitecombe, D., et al., Nature Biotechnology, 17:804-807, 1999.
Aktipis, S., et al., Biochemistry 14:326-331, 1975.
Douthart, R.J., et al., Biochemistry 12:214-220, 1973.
Nuovo, G.J., et al., J. Histochem. Cytochem. 47:273-279, 1999.
Gundry, C.N., et al., Genetic Testing, 3:365-370, 1999.
Lipsky RH, et al., "DNA melting analysis for detection of single nucleotide polymorphisms". Clin Chem. Apr. 2001;47(4):635-44.
Hermann, M.G. et al., Clin. Chem., 44(3): 425-428, 2000.
Millward, H., et al., Clin. Chem., 48(8): 1321-1328, 2003.
Li, Q., et al., Nuc. Acid Res., 30(2): e5, 2002.
"Heteroduplex Panel Analysis, A Novel Method for Genetic Identification of *Aspergillus* Section *Flavi* Strains," Kumeda et al., Appl. Environ. Microbiol., vol. 67(9), Sep. 2001.
Lay et al., "Real-Time Fluorescence Genotyping of Factor V Leiden During Rapid-Cycle PCT," Clinical Chemistry, vol. 43, No. 12, pp. 2262-2267, 1997.
Bernard et al., "Integrated Amplification and Detection of the C677T Point Mutation in the Methyelenetetrahydrofolate Reductase Gene by Fluorescence Resonance Energy Transfer and Probe Melting Curves," Analytical Biochemistry vol. 255, pp. 101-107, 1998.
Morrison et al., "Quantification of Low-Copy Transcripts by Continuous SYBR® Green 1 Monitoring During Amplification," BioTechniques, vol. 24, No. 6, pp. 954-962, 1998.

* cited by examiner

GENOTYPING BY AMPLICON MELTING CURVE ANALYSIS

This application claims priority under 35 U.S.C. §119(e) to U.S. Provisional Patent Application Ser. Nos. 60/380,354, filed May 13, 2002, and 60/386,975, filed Jun. 7, 2002 the disclosures of which are hereby incorporated by reference herein.

US GOVERNMENT RIGHTS

This invention was made with United States Government support under Grant Nos. GM58983 and GM60063, awarded by the NIH. The United States Government has certain rights in the invention.

BACKGROUND AND SUMMARY OF THE INVENTION

Most conventional methods for detecting unexpected sequence variations require gel electrophoresis after PCR. These include single-strand conformation polymorphism (Orita, O., et al., Proc. Natl. Acad. Sci. USA. 86:2766-2770, 1989), heteroduplex migration analysis (Nataraj, A. J., et al., Electrophoresis. 20:1177-1185, 1999), denaturing gradient gel electrophoresis (Abrams, E. S., et al., Genomics 7:463-475, 1990), temperature gradient gel electrophoresis (Wartell, R. M., et al., J. Chromatogr. A. 806:169-185, 1998), and enzyme cleavage methods (Hawkins G. A., et al., Electrophoresis, 20:1171-1176, 1999). Identifying new mutations by DNA sequencing also requires multiple steps, including cycle sequencing and gel electrophoresis. Denaturing high-performance liquid chromatography (Narayanaswami, G., et al., Genetic Testing. 5:9-16, 2001) is a more recent method, but requires sampling and injection after PCR.

Recently, homogeneous fluorescent methods have been reported for mutation scanning. SYBR Green I is a double stranded DNA binding dye that is often used to monitor product formation (Wittwer C. T., et al., BioTechniques, 22:130-138, 1997) and melting temperature (Ririe K. M., et al., Anal. Biochem, 245:154-160, 1997) in real-time PCR. Following PCR product purification and addition of SYBR Green I, single nucleotide polymorphisms have been detected in up to 167 bp products by melting curve profiles (Lipsky, R. H., et al., Clin. Chem. 47:635-644, 2001). However, the high concentration of SYBR Green I used inhibits PCR (Wittwer C. T., et al., Methods, 25:430-442, 2001), so the dye was added after amplification. In addition, PCR product purification was necessary, further limiting the possibility of real-time analysis. In another report, GC clamping was used with SYBR Green I to detect single nucleotide polymorphisms in up to 212 bp products (Elenitoba-Johnson, K. S. J., et al., Am. J. Pathol. 159:845-853, 2001, and U.S. Pat. No. 6,346,386). However, after PCR, the solution required adjustment to 12M in urea before the melting analysis. In both cases, sample additions after PCR were necessary. Any manipulation of the sample increases the risk of PCR product carryover into subsequent reactions.

Another homogeneous fluorescent approach is to use real-time hybridization probes (Wittwer C. T., et al., BioTechniques, 22:130-138, 1997). These probes can detect any mutation under the probe by melting temperature shifts. Multiple single-labeled hybridization probes have been tiled across amplicons to scan for p53 mutations by Tm multiplexing (Millward H., et al., Clin. Chem, in press, 2002).

There are a number of designs for PCR primers that facilitate change in fluorescence when the primers are incorporated into the PCR product. These designs include but are not limited to the double-stranded displacement primer (Li, Q., et al., Nucleic Acids Res., 30: e5, 2002) whose fluorescence is quenched initially by an acceptor fluorophore placed on the complementary oligonucleotide that dissociates upon PCR, releasing the fluorescence signal, and the Scorpion primer (Whitecombe, D., et al., Nature Biotechnology, 17:804-807, 1999) which has a stem-loop tail that brings the reporter close to a quencher prior to PCR, but releases the signal by denaturation and incorporation into the PCR product. Most of these designs aim primarily to detect amplification. In some cases, genotyping had been performed by allele-specific amplification. None of these references teach the use of melting analysis and differentiation of sequence variation by melting temperature.

PCR primers fluorescently labeled at the 5' residue have already been discussed to distinguish between different analytes based on differences in melting temperature (U.S. patent application 20010000175 Kurane et al). However, according to the teaching of Kurane, it is impossible to discriminate between small differences of sequence variants, since the results of a melting curve analysis very strongly depend on the concentration of the target nucleic acid. Therefore, prior to the present invention, it has never been shown that these, or other forms of labeled primers, can be used to detect small sequence variations or heteroduplexes in amplified product by melting analysis.

In one aspect, the present invention is directed to a simple and sensitive real time PCR method for mutation scanning and identification of small sequence variations on a broad range of sequences. By using a 5'-labeled PCR primer, single-nucleotide polymorphisms and other small sequence variances in PCR products can be detected by the melting profiles of the amplified product. These melting profiles show when a heteroduplex is present, and the melting profiles can be used for real time mutation scanning without any need for additions or manipulations after PCR. In addition, different homozygotes can often be distinguished from each other, as well as different heterozygotes. That is, genotyping is often possible with the methods of the present invention. Finally, subtyping of organisms as well as genetic haplotyping are possible based on the inventive method.

In one embodiment, the invention provides a method for sequence variation scanning that requires only PCR and amplicon melting analysis without any intermediate processing. At least one of the PCR primers is fluorescently-labeled such that a change in fluorescence occurs when the amplicon is melted. Heteroduplexes are detected as a low-temperature shoulder and broadening of the peak on derivative melting curve plots. Heteroduplex detection is increased by denaturation, followed by rapid cooling (>2° C./s) before melting, low cation concentration, and rapid heating during melting (0.1-0.5° C./s). In an alternative embodiment, two unlabeled primers can be used with a third labeled indicator primer that has sequences homologous to a universal tail added to one of the unlabeled primers.

In various embodiments, the methods of the present invention have been used to detect polymorphisms in HTR2A (T102C), beta-globin (Hb S, C and E), apo E (2/2, 2/3, 2/4, 3/3, 3/4, and 4/4), and CFTR (F508del, F508C, I507del, I506V). In most cases, different homozygotes could be distinguished from each other by melting temperature (Tm), heterozygotes could be distinguished from homozygotes by a low temperature shoulder and a more gradual transition, and different heterozygotes could be differentiated from other heterozygotes by the shape of the fluorescent melting curve.

Amplicon sizes varied from 44-303 bp. The presence of less than 5% variant DNA (differing at a single base in a 243 bp amplicon) was detected.

DETAILED DESCRIPTION

Homogeneous real-time mutation scanning has been elusive. Double strand specific DNA dyes seem like ideal candidates. SYBR Green I in particular is used extensively in melting analysis and shows a large change in fluorescence during PCR (Wittwer C. T., et al., Real-Time PCR, in Diagnostic Molecular Microbiology: Principles and Applications. D Persing, et al., eds., ASM Press, in press, 2002). However, as the temperature is increased during melting curve acquisition, SYBR Green I is freed from heteroduplexes that melt at low temperature and re-associates with homoduplexes that melt at higher temperatures. Ethidium bromide also has been reported to redistribute during melting (Aktipis, S., et al., Biochemistry 14:326-331, 1975). Because SYBR Green I is not limiting at concentrations compatible with PCR, re-association does not result in a net change in fluorescence during the heteroduplex transition (FIG. 1). Another problem with solution heteroduplex detection by melting analysis is that low melting heteroduplex strands may re-associate with their perfect complement. Because of the high concentration of PCR product at the end of PCR, this re-association may happen rapidly, again resulting in no net change in fluorescence during the transition of the heteroduplex. DNA dyes tend to shift the Tm to higher values and broaden the width of the melting transition (Douthart, R. J., et al., Biochemistry 12:214-220, 1973). Analytes with high Tms may be difficult to denature, and broader transitions may lower the resolution of the melting curve.

Figure 2A:
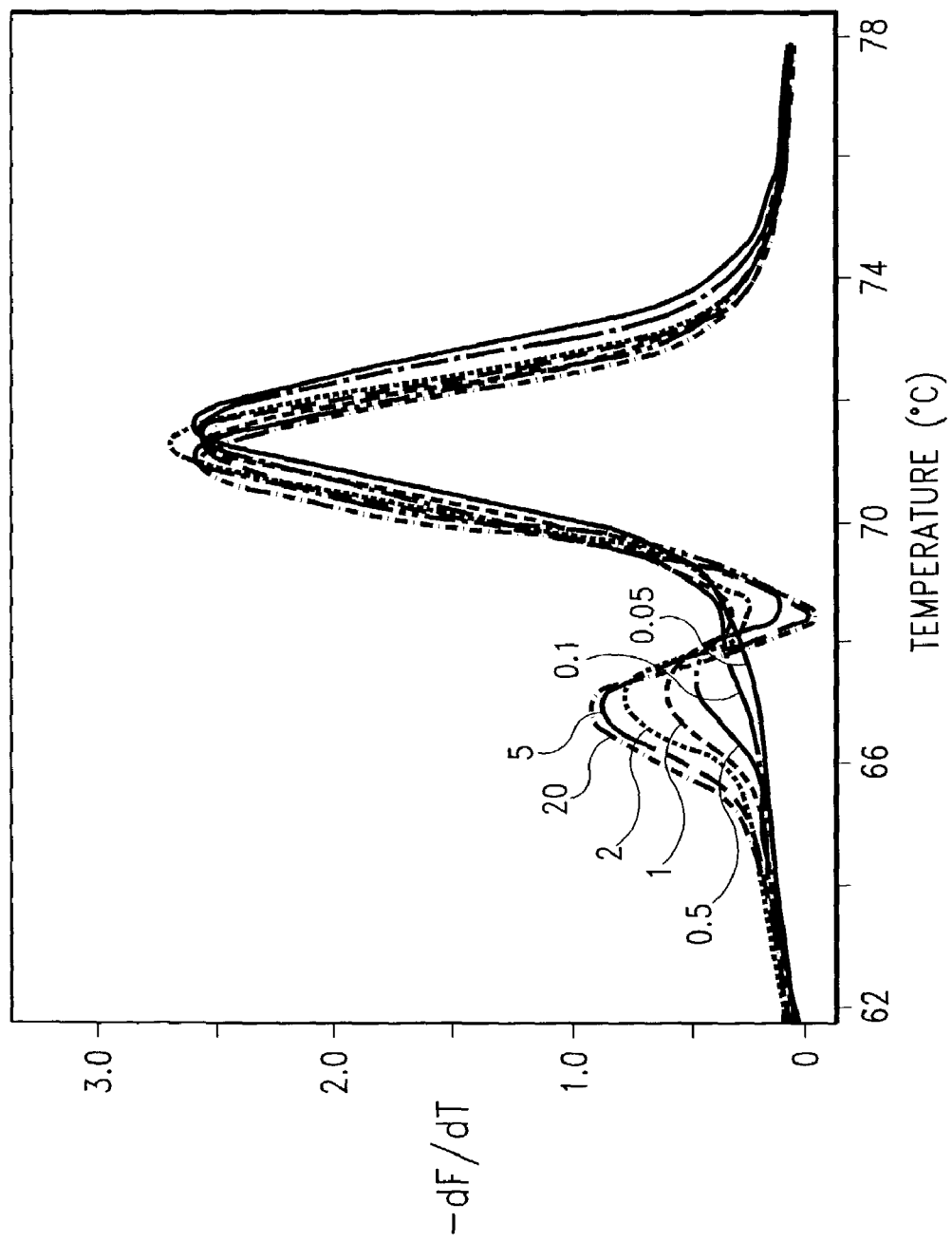
FIG. 2A shows heteroduplex formation is greater with rapid cooling. Heterozygous F508del DNA at the CFTR locus was PCR amplified with one labeled primer. The samples were denatured, cooled at different rates, and heteroduplexes were observed during melting on the LightCycler.
Figure 2B:
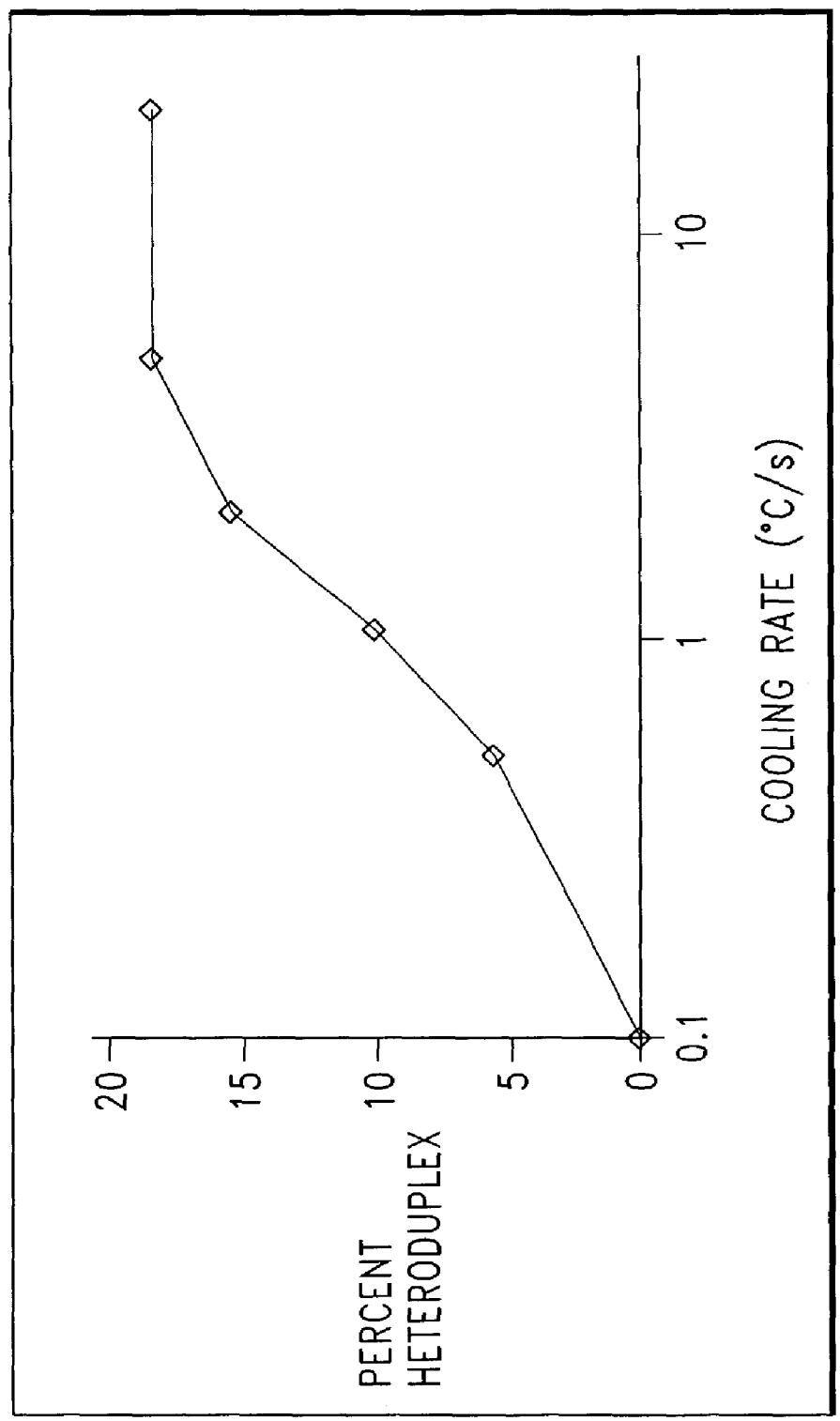
FIG. 2B diagrams the effect of cooling rate (° C./s) on heteroduplex formation.

The use of labeled primers according to the present invention, however, avoids problems associated with the use of untethered double-stranded DNA dyes for mutation scanning. There is no dye to redistribute, no increase in Tm and no broadening of the melting transition. Where heteroduplexes are a concern, the likelihood of re-association may be reduced by limiting the time the solution is at a temperature where re-association is likely to occur. Re-association is particularly likely when the temperature is between the Tms of the heteroduplexes and the homoduplexes. This time period can be limited by rapid cooling before melting and rapid heating during melting. Rapid heating also reduces nascent priming during the melting process and thereby disfavors the net decrease of heteroduplexes. In addition, nucleic acid annealing rates are lower at lower cation concentrations. These theoretical expectations are in line with the obtained results. More pronounced heteroduplex peaks are present with rapid cooling (FIG. 2), rapid heating (FIG. 3) and low Mg++ concentration (FIG. 4). Practical limitations to rapid heating include difficulty with maintaining temperature homogeneity within the sample, fewer fluorescence acquisitions, and broadening of the melting transition.

The data may be presented either as fluorescence vs temperature plots or as first derivative plots of fluorescence vs temperature. The two plots are interchangeable, but each focuses the viewer's attention on different aspects of the data. The melting peak (or Tm) is best viewed on derivative plots. However, the broadening of the transition and appearance of low melting transitions are easier to observe on fluorescence vs temperature plots.

Labeled primers that change fluorescence with amplicon melting have potential for both unknown mutation scanning and specific genotyping. Consideration of domain melting is important in these applications. Unlike denaturing gradient gel electrophoresis, the informative domain is not necessarily the first melting domain, but is the domain that includes the labeled primer. If the polymorphism is not in the melting domain of the labeled primer, the polymorphism will only be detected with reduced sensitivity. An extreme example of this is given in FIG. 14, where the polymorphism farthest away from the labeled primer at the apoE locus is not detected at all. Apparently, the mismatch melts before the domain that includes the labeled primer. There are at least 2 approaches to correct this limitation. A GC clamp can be added to the unlabeled primer, forcing the rest of the amplicon to melt as one domain (Abrams, E. S., et al., Genomics 7:463-475, 1990; 11). Alternately, both primers can be labeled, preferably with different dyes that have spectrally distinct emissions. Color multiplexing techniques (Wittwer C. T., et al., Methods, 25:430-442, 2001) can be used to follow the melting of both labels, monitoring both sides of the amplicon. Other approaches to correct this limitation are within the scope of this invention.

Mutation scanning techniques can be judged by their mutation detection sensitivity (Nataraj, A. J., et al., Electrophoresis. 20:1177-1185, 1999). Detection sensitivity depends on the amplicon size and the stability distribution within the amplicon. According to the present methods, a mutation was missed that was 175 bp away from the labeled end. It may be that heteroduplexes from polymorphisms near the end of an amplicon are prone to "breathing" or melting before the majority of the amplicon. These end polymorphisms according to the invention can be detected by introducing a GC clamp, or by labeling both ends of the amplicon. Detection might still fail if an internal domain melts before the ends. However, when both ends are covered, all heterozygous sequence variations within most amplicons of up to 300, probably up to 500, and possibly up to 800 bp in length may be detected.

Taken together, one embodiment of the present invention is directed to a method for analyzing a target nucleic acid in a nucleic acid sample, comprising a) amplifying the target nucleic acid in a nucleic acid amplification reaction mixture to generate an amplification product, the amplification reaction mixture comprising
  aa) a polymerase,
  ab) deoxynucleoside triphosphates or functional analogues,
  ac) a plurality of primers comprising at least a first primer and a second primer,
    the first primer being sufficiently complementary to the target nucleic acid to hybridize therewith and initiate template dependent synthesis by the polymerase,
    the second primer being sufficiently complementary to the complement of the target nucleic acid to hybridize therewith and initiate template dependent synthesis by the polymerase, characterized in that at least one primer is labeled with a fluorescent compound, the labeled primer being selected from the group consisting of
      i) the first primer,
      ii) the second primer,
      iii) and an indicator primer, the indicator primer being sufficiently complementary
        to hybridize to a DNA fragment that is amplified only if the first and the second primer are used, and
        to initiate synthesis by the polymerase,
      wherein the labeled primer becomes incorporated into a strand of the amplification product, and
b) monitoring change in fluorescence emission resulting from dissociation of the labeled strand of the amplification product from its complementary strand.

The first illustrated embodiment is a method for analyzing the sequence of a target nucleic acid, comprising a) amplifying said target nucleic acid in a nucleic acid amplification reaction mixture to generate an amplification product, said amplification reaction mixture comprising
  aa) a polymerase,
  ab) deoxynucleoside triphosphates or functional analogues,
  ac) a pair of amplification primers comprising a first primer and a second primer, said first primer being sufficiently complementary to said target nucleic acid to hybridize therewith and initiate template dependent synthesis by the polymerase,
  said second primer being sufficiently complementary to the complement of said target nucleic acid to hybridize therewith and initiate template dependent synthesis by the polymerase, characterized in that either one or both amplification primers are labeled with a fluorescent entity which is not in a FRET-donor-acceptor relationship within any other fluorescent entity that may be present in the sample, b) denaturing said amplification product into single strands and subsequently renature said single strands to form a double stranded product, and c) subjecting said amplification mixture containing the amplified target sequence to a double stranded DNA denaturing gradient and simultaneously monitoring fluorescence emission.

Summarizing, for this first illustrated embodiment, conventional PCR amplification primers may be used, with the provision that either one or both primers are labeled with the same or a different fluorescent compound.

In a specific embodiment, 2 or more target nucleic acids are amplified in a multiplex approach using 2 or more pairs of amplification primers, wherein either one or both primers comprising a pair of amplification primers are labeled. In this case, each primer pair is illustratively labeled with a different fluorescent compound having a distinguishable fluorescence emission spectrum as compared to the remaining primer pairs. This allows for discrimination of fluorescence signaling with respect to each target nucleic acid sequence that is being analyzed.

The second illustrated embodiment is a method for analyzing the sequence of a target nucleic acid, comprising a) amplifying said target nucleic acid in a nucleic acid amplification reaction mixture to generate an amplification product, said amplification reaction mixture comprising
   aa) a polymerase,
   ab) deoxynucleoside triphosphates or functional analogues,
   ac) a pair of amplification primers, comprising a first primer and a second primer,
      said first primer being sufficiently complementary to said target nucleic acid to hybridize therewith and initiate template dependent synthesis by the polymerase,
      said second primer being sufficiently complementary to the complement of said target nucleic acid to hybridize therewith and initiate template dependent synthesis by the DNA polymerase,
   ad) an indicator primer labeled with a fluorescent entity which is not in a FRET-donor-acceptor relationship within any other fluorescent entity that may be present in the sample, said indicator primer being sufficiently complementary
      to hybridize to the DNA fragment that is amplified with said pair of amplification primers, and
      initiate synthesis by the polymerase,
b) denaturing said amplification product into single strands and subsequently renaturing said single strands to form a double stranded product, and
c) subjecting said amplification mixture containing the amplified target sequences to a double stranded DNA denaturing gradient and simultaneously monitoring fluorescence emission.

Summarizing, for this second illustrated embodiment, two conventional PCR amplification primers are used together with a third labeled indicator primer that is capable of hybridizing with the amplified target sequence. Also in case of the second basic embodiment, 2 or more target nucleic acids may be amplified in a multiplex approach using 2 or more pairs of unlabeled amplification primers.

In one specific embodiment, the labeled primer is capable of hybridizing to the target sequences because its sequence is chosen in such a way that it matches either perfectly or at least imperfectly with the target DNA. For the multiplex approach, such a primer may be designed if different genes are amplified that share at least one consensus region. In this case, the indicator sequence may be chosen appropriately to hybridize with exactly that region.

In another preferred embodiment of the invention, the indicator sequence may be introduced into the amplicons through the amplification primers that are used. In this case, at least one primer of each pair of amplification primers includes at least a first and a second segment, the first segment being sufficiently complementary to a target nucleic acid to hybridize therewith, the second segment being sufficiently homologous to the indicator sequence of the indicator primer, and the second segment being located more proximal to the 5' end of the primer as compared to the first segment. Under these circumstances, only one type of labeled amplification primer is required.

In the context of this application, the term "homologous" shall mean that the respective primer hybridizes to the complement of the homologous sequence under standard conditions within a standard PCR reaction mixture and is capable of initiating DNA synthesis by a polymerase appropriate for use in PCR amplification. Furthermore, "polymerase" means any polymerase usable in nucleic acid amplification, illustratively a DNA dependent DNA polymerase.

The ability to use an indicator universal primer means that only one fluorescently-labeled oligonucleotide needs to be synthesized to scan for sequence changes at many targets. One primer from each target is modified to include the indicator sequence. Multiple rounds of PCR incorporate the labeled primer into the final amplicon. Reactions require 3 oligonucleotides instead of 2, but the same fluorescently-labeled oligonucleotide can be used for all targets even in different assays that are performed independently from each other. In an illustrated embodiment, the universal primer lacks sufficient homology with the target sequence that the universal primer cannot hybridize to the target sequence and initiate synthesis.

Depending on the type of assay and the type of fluorescent compound that is actually used, fluorescence emission may either increase or decrease when an amplified product incorporating the labeled primer dissociates or melts. According to the present invention, a labeled primer is selected such that modification of fluorescence emission is caused primarily by dissociation or melting of double-stranded nucleic acids to which the fluorescent compound is attached.

In the methods of this invention, fluorescence is monitored as a function of a denaturing gradient. Independent from the type of gradient, however, what is actually monitored is the change in fluorescence caused by the dissociation of the two strands of the double-stranded amplification product, observed from the site where the fluorescent label has been incorporated into the PCR product.

The denaturing gradient may be a thermal gradient. In other words, the invention is illustratively directed to a method, characterized in that during or subsequent to the PCR amplification using an appropriately labeled primer, temperature dependent fluorescence is monitored. Alternatively, the denaturing gradient may be a gradient of chaotrophes. This monitoring may be performed separate from the amplification process, for example on a device dedicated to DNA denaturation analysis and fluorescence monitoring or with any other device known in the art, such as denaturing gradient gel electrophoresis. It is often desirable, however, if the monitoring of temperature dependent fluorescence is part of a homogeneous assay format such that PCR amplification and monitoring temperature dependent fluorescence are carried out in the same reaction chamber without intermediate opening of the reaction chamber.

It is known in the art (see U.S. Pat. No. 6,174,670, herein incorporated by reference) that melting analysis may be obtained by monitoring temperature-dependent fluorescence during melting. Usually, melting curve analyses are performed as slowly as possible in order to generate precise and highly reproducible data, to obtain an exact determination of the melting point, which is defined as the maximum of the first derivative of a temperature versus fluorescence plot. However, if the selected time parameters are comparatively short, certain advantages may be seen. Illustratively, the temperature transition within the cooling phase is at least 0.1° C./s, preferably at least 1° C./s and most preferably at least 5°

C./s. Also illustratively, the temperature transition within the melting phase is at least 0.05° C./s, preferably at least 0.2° C./s, and most preferably at least 0.4° C./s. Depending on the application, short cooling phases and short melting phases may be combined.

Illustratively, fluorescent signaling may be provided by nucleobase quenching (von Ahsen N., Labeled primers for mutation scanning: making diagnostic use of the nucleobase quenching effect. Clin. Chem. 49:355-6, 2003), wherein the effects of neighboring nucleobases affect fluorescent emission. In illustrative examples of nucleobase quenching, fluorescent signaling increases upon hybridization of a PCR amplicon having a label incorporated therein. Similarly, fluorescent signaling illustratively decreases upon melting of the PCR amplicon. However, depending on the type of fluorescent dye used and the neighboring bases, it is also possible that a significant signal decrease is observed during hybridization, with a corresponding increase upon melting. As long that it is understood that some dyes will exhibit increased fluorescence upon melting and others will exhibit decreased fluorescence, a wide variety of fluorescent dyes can be used to label the primers. Fluorescein, Oregon Green, BODIPY-FL, Cy5, and Texas Red all give good signals.

Most dyes attached to oligonucleotides change fluorescence when the oligonucleotide hybridizes, and change fluorescence in the opposite direction when the duplex melts. In particular, Oregon Green attached to a G residue on the primer through SimpleProbe chemistry (Idaho Technology Biochem) results in a nice decrease in fluorescence with amplicon melting, while BODIPY-FL attached to a C residue on the primer results in a nice increase in fluorescence with melting. The only requirement for the fluorescent label is that its fluorescence intensity changes when the nucleic acid to which it is attached is hybridized to a complementary or semi-complementary strand.

Thus, in a specific embodiment of the invention the nucleotide residue carrying the fluorescent compound is a G residue. Depending on the fluorescent compound used, this often results in a decreased fluorescent signal with melting. Even more specifically, the G residue may be labeled with Oregon Green, although other fluorescent dyes may be used within the scope of this disclosure.

In another specific embodiment, the nucleotide residue carrying the fluorescent compound is a C residue. More specifically, the C residue may carry a BOPIDY-FL as the fluorescent compound, although other fluorescent dyes may be used within the scope of this disclosure.

In general, when the dye is attached to a G residue, fluorescence is quenched when the nucleic acid is in a single-strand conformation. Upon duplex formation, this effect is partly removed, but is restored again when the duplex dissociates biasing the fluorescence to decrease. Conversely, dyes attached to C residues usually increase in fluorescence upon melting, presumably because they lose the proximity with the complementary G. However, whether fluorescence increases or decreases with melting also depends on the specific fluorescent dye and on the molecular linker attaching the fluorescent dye to the oligonucleotide. For example, the magnitude and even the direction of the fluorescence change observed with melting depends on the molecular linker that attaches fluorescein to the primer. When fluorescein is linked to the terminal 5' phosphate (or directly to the nucleobase) through an isothiocyanate linkage to A, T, or G, the direction is usually negative and the magnitude is small. With a carboxyfluorescein linkage, the direction is also negative but the magnitude is substantially larger. When the linkage is through a C residue and fluorescein is attached through an isothiocyanate linkage, the direction is positive. However, with a carboxyfluorescein linkage, the direction is reversed and becomes weakly negative. In another example, the fluorescent label is attached through a base analog, illustratively a nitroindole, which biases the fluorescence change to decrease with melting. Furthermore, it is advantageous if the primer to be labeled is labeled at its 5' end with the respective fluorescent compound, since 5' labeling of oligonucleotides may be performed easily and inexpensively by many different methods which are known in the art. It is understood that other configurations are within the scope of this invention. See, e.g., U.S. application publication no. 20030022177, Wittwer et al., herein incorporated by reference. Illustrative examples are provided below in Table 1.

TABLE 1

| Dye attached to 5' end of oligonucleotide | Oligonucleotide sequence[1] | Amplicon melting change (%)[2] | |
|---|---|---|---|
| 6-carboxyfluorescein[3] | TX | −31 | (synthetic) |
| | AX | −25 | (synthetic) |
| | CX | −5 | (synthetic) |
| | X | −10 | (synthetic) |
| | GX | −20 | (synthetic) |
| | GGX | −26 | (synthetic) |
| | nGX | −50 | (synthetic) |
| | nCX | −39 | (synthetic) |
| | GGX | −29 | |
| 5-fluorescein-ITC[4] | GGX | 0 | |
| | CX | +34 | (synthetic) |
| | pX | −35 | (synthetic) |
| | nFX[5] | −57 | (synthetic) |
| Oregon Green 488 | TX | −42 | (synthetic) |
| | AX | −31 | (synthetic) |
| | CX | −3 | (synthetic) |
| | X | −4 | (synthetic) |
| | GX | −24 | (synthetic) |
| | GGX | −20 | (synthetic) |
| | GGX | −21 | |
| | GGY | −26 | |
| | nGGY | −39 | |
| Oregon Green 500 | GGY | +7 | |
| | nGGY | −22 | |
| Oregon Green 514 | GGY | −14 | |
| | nGGY | −23 | |
| JOE | GGX | −8 | |
| 6G-HEX | GGX | −2 | |
| Carboxyrhodamine X | GX | −40 | |
| Rhodamine 6G | GGX | +5 | |
| Rhodamine X | GGX | +4 | |
| BODIPY-FL | CCX | +61 | |
| | CCTGGY | +69 | |

[1]n is a 5-nitroindole base analog; p is a 3-nitropyrrole base analog; F is the fluorophore when it is not on the 5' end; X is 5'GCTGCACGCTGAGGT3' (SEQ ID NO:1) (the target-independent primer tail mentioned in the text); Y is 5'CACCATTAAAGAAAATAT3' (SEQ ID NO:2) (one of the primers for the CFTR loci)
[2]DNA fragments were amplified similarly to other examples discussed below, and melting curve analyses were performed. In some cases, unlabeled complementary strands to the labeled oligonucleotides were synthesized, mixed in excess and annealed prior to melting (designated as "synthetic"). Most of the synthetic duplexes had blunt ends. However, when the fluorophore was attached to a base analog, the complementary strand was made to pair only up to the conventional base adjacent the base analog (or next to the fluorophore in the case described in note 5). The percent change in fluorescence occurring from dissociation of the double strand was determined as follows: linear baselines, before and after the melting transition, were extrapolated to the midpoint of the melting transition (Tm). The intersection of these baselines with the Tm define maximum and minimum fluorescence values characteristic of the transition. The percent change relative to the minimum fluorescence value is calculated as (MAX−MIN)/MIN × 100 if the fluorescence increases with melting, and (MIN−MAX)/MIN × 100 if the fluorescence decreases.

TABLE 1-continued

| Dye attached to 5' end of oligonucleotide | Oligonucleotide sequence[1] | Amplicon melting change (%)[2] |
|---|---|---|

[3]Structure:

[structure of fluorescein derivative with COOH group and amide-linked phosphate]

[4]Structure:

[structure of fluorescein derivative with COOH group and thiourea-linked phosphate with OH]

[5]In this case the fluorophore was not on the terminal 5' end but between the 5' base analog and a G. The complementary strand supplied only paired up to this G leaving an overhang of the fluorophore and the base analog.

In the above-described embodiments, the fluorescence increases or decreases without changing the distance between any dyes that are in a fluorescence resonance energy transfer (FRET) relationship. In the context of the present invention, the term "FRET-donor-acceptor relationship" means fluorescence resonance energy transfer between a donor and an acceptor compound that results in observable fluorescence emission from the acceptor compound. According to the present invention, the modification of fluorescence emission is caused by a nucleobase quenching effect, not by changing the distance between dyes in a FRET relationship. However, FRET relationships that do not change during melting are within the scope of this invention, such as primers labeled with composite-FRET dyes such as BigDyes (Applied Biosystems) which are conjugates of donor and acceptor compounds constituting a FRET pair, are within the scope of this invention as long as the change in fluorescent signal is caused primarily by melting of the PCR product and not by a change in the FRET relationship. Similarly, double-stranded displacement primers having a reporter and a quencher (a FRET pair) on opposite strands are within the scope of this invention, as long as the primer carrying the reporter dye acts as the primary agent to produce melting signals of PCR product without involving a change in the FRET relationship.

In another embodiment, the fluorescent compound is a double-stranded nucleic acid binding dye that is covalently attached to one or more strands of the target nucleic acid, illustratively as the fluorescent label attached to one of the primers used in nucleic acid amplification.

Another aspect of the invention is to introduce an artificial GC clamp by means of an appropriate design of the unlabeled primer. Consequently, the invention is also directed to an illustrated embodiment wherein only one primer is labeled, further characterized in that the unlabeled primer has a 5' tail of 3-30 G or C residues, and preferably 5-20 residues, which tail is not complementary to the target nucleic acid.

While reference is made to PCR, it is understood that other methods of amplification may be used within the scope of this invention, as are known in the art. Such methods include, but are not limited to, PCR with reverse transcription (RT-PCR); strand displacement amplification (SDA); nucleic acid sequence-based amplification (NASBA); transcription-mediated amplification (TMA); rolling circle amplification (RCA), and the like. While not always accomplished in a "homogeneous" process, these methods may further be combined with processes such as restriction enzyme cleavage, strand-specific end-labeling, strand-specific capture and immobilization, or the like, prior to melting analysis. Also, while reference is made to amplification and post-amplification analysis, the melting temperature analysis according to this disclosure may be performed on nucleic acids that are obtained by other means, such as restriction fragments. The restrictions fragment may itself be end-labeled, or a labeled reference strand may be mixed and subjected to melting temperature analysis, according to the methods described herein.

Yet another aspect of the invention relates to a reaction mixture for performing one of the methods disclosed above. More precisely, a reaction mixture according to the invention comprises a polymerase,
  deoxynucleoside triphosphates or functional analogues,
  a plurality of primers comprising at least a first primer and a second primer,
    the first primer being sufficiently complementary to the target nucleic acid to hybridize therewith and initiate template dependent synthesis by the polymerase,
    the second primer being sufficiently complementary to the complement of the target nucleic acid to hybridize therewith and initiate template dependent synthesis by the polymerase,
  characterized in that at least one primer is labeled with a fluorescent compound, the labeled primer being selected from the group consisting of
    the first primer,
    the second primer, and
    an indicator primer, the indicator primer being sufficiently complementary
      to hybridize to a DNA fragment that is amplified only if the first and the second primer are used, and
      to initiate synthesis by the polymerase,
  wherein the labeled primer becomes incorporated into a strand of the amplification product, and wherein the fluorescent entity is not in a FRET-donor-acceptor relationship with any other fluorescent entity that may be present in the sample during amplification of a target nucleic acid.

In addition, the present invention is directed to a kit for preparing the reaction mixtures disclosed above. Such a kit may comprise several or all of the following compounds:
  a polymerase,
  deoxynucleotides or analogs,
  buffers,
  a labeled primer, and/or
  one or more unlabeled primers.

The present invention may be used to analyze any kind of sequence variations and thus can be applied to different technical fields:

In a first major aspect, the present invention relates to the use of the methods disclosed above for analyzing the sequence of at least one or more target nucleic acids for the presence or absence of a polymorphism, including but not limited to the detection of single nucleotide polymorphisms (SNPs). Under appropriate experimental conditions, the shapes and positions of melting curves are highly reproducible. It is thus also possible to analyze sequences for the presence or absence of previously unknown polymorphisms, which may even result in the detection of new sequence variants.

A second aspect of the present invention relates to the usage of the methods and compositions disclosed above for the determination of a genotype of microorganisms and viruses, including but not limited to the genotype determination of infectious disease parameters such as HIV, HCV, or HPV. As it is known in the art, sometimes there exist only minor sequence differences between different strains of infectious agents which nevertheless result in different pathogenic consequences. Therefore, the new invention provides a sensitive tool for early and rapid genotype determination, which facilitates and accelerates selection of an appropriate medical treatment of infectious diseases.

A still further aspect of the present invention relates to the usage of the methods and compositions disclosed above for determination of an allelic status. For example, the ability to distinguish homozygous sequence variants is useful. ApoE 2/2, 3/3, and 4/4 are easily distinguishable via melting curve analysis. While Hb AA and Hb SS are more difficult to distinguish, even these homozygous variants may be distinguished. It is noted that the ApoE homozygotes all differ by G/C:A/T substitutions, while Hb AA and Hb SS differ only by a A/T:T/A substitution. According to the invention, however, one way to detect homozygous variants with the same Tm as wild type is to mix wild type with the unknown DNA. If a homozygous variant is present, the resulting heteroduplexes will produce the characteristic low temperature shoulders and broad peaks. As it is possible to detect a variant DNA that is present in amount of less than 5% of the total analyte concentration (e.g. FIG. 13B), the technique is resilient to variation in DNA concentration.

Different heterozygotes are often distinguishable because each heterozygote produces two different homoduplexes and two different heteroduplexes. Each duplex has a unique melting temperature and the combination of all four duplexes produces the observed melting profile. For example, the beta-globin SC heterozygote has a longer low temperature shoulder than other heterozygotes (FIGS. 8 and 9) because the SC heteroduplexes are mismatched in 2 adjacent positions, compared to single mismatches in the other heterozygotes. The various shapes of the melting curves are determined by the stability and/or the kinetic melting rates of the homoduplexes and heteroduplexes present. Under constant experimental conditions, the melting curves are easily determined and reproducible.

The invention is also directed to a method for determining the allelic status of a target gene in a DNA specimen. With the methods of the present disclosure, it is possible to discriminate easily between a homozygous and a heterozygous state, and it is even possible to distinguish between different homozygotes. While homozygotes may be distinguished with the methods presented herein, it is within the scope of the present invention to mix an unknown DNA specimen with known homozygous DNA, either prior to or subsequent to the amplification reaction itself. Such may provide for easier homozygote determination.

In yet another embodiment of this invention, methods are provided for identifying a sequence variant of a target nucleic acid in a nucleic acid sample, the target nucleic acid comprising a first strand and a generally complementary second strand, wherein the first strand is labeled with a fluorescent compound, the method comprising the steps of denaturing the target nucleic acid into single strands, cooling the sample to renature the single strands to form a double stranded product, wherein the cooling rate is at least 0.1° C./s preferably at least 0.2° C./s, and most preferably at least 0.4° C./s, subjecting the sample to a thermal gradient and simultaneously monitoring change in fluorescence emission resulting from dissociation of the labeled strand of the amplification product from its complementary strand, wherein temperature transition within the thermal gradient is at least 0.05° C./s, preferably at least 0.2° C./s, and most preferably at least 0.4° C./s.

It is understood that in this embodiment, sequence variants may be detected without amplification. Alternatively, such methods may be used subsequent to amplification.

EXAMPLES

PCR Protocol

Labeled and unlabeled oligonucleotides were obtained from IT Biochem, Operon, or Synthegen. Purity was assessed by absorbance as previously described (Wittwer C. T., et al., Methods, 25:430-442, 2001). PCR was performed in 10 μl volumes in a Roche LightCycler with programmed transitions of 20° C./sec unless otherwise indicated. The amplification mixture included 50 ng of genomic DNA as template, 200 uM of each dNTP, 0.4 U of KlenTaq1 polymerase (AB Peptides, St. Louis, Mo.), 88 ng of TaqStart antibody (ClonTech), 3 mM $MgCl_2$, 50 mM Tris, pH 8.3, 500 μg/ml bovine serum albumin, and 0.5 μM primers unless indicated otherwise. When SYBR Green I was used as the indicator instead of labeled primers, a 1:30,000 final dilution from the Molecular Probes (Eugene, Oreg.) stock was used. Melting analysis was usually performed on the LightCycler immediately after cycling. In some cases, a high resolution melting curve was obtained by placing the capillary sample in a boiling water bath for 3 sec, cooling in ice water for 3 sec, and then heating the sample at 0.3° C./sec in a surrounding aluminum cylinder with 16-bit data acquisition of temperature from a thermocouple and fluorescence by epi-illumination of the capillary tip.

Genotyping at the Cystic Fibrosis Transconductance Regulator (CFTR) Locus with Labeled Primers or SYBR Green I.

A 44 base-pair fragment of the CFTR gene was amplified with the primers GGCACCATTAAAGAAAATAT (SEQ ID NO:3) and TCATCATAGGAAACACCA (SEQ ID NO:4). The forward primer was either 5'-labeled as an Oregon Green SimpleProbe (Idaho Technology) or SYBR Green I was included in the reaction. The primers surround the mutational hot spot containing the F508del, I507del, F508C mutations. PCR was performed by cycling 40 times between 85° C. and 58° C. (0 sec holds). A final melting cycle was performed on the LightCycler by heating to 95° C., cooling to 55° C. then collecting fluorescence continuously at a ramping rate of 0.2° C./sec.

Analysis of the Effects of Cooling Rate, Heating Rate, and Mg++ Concentration on Heteroduplex Analysis.

Using the 44 bp amplicon given above, the effects of cooling and heating rates and Mg++ concentration were studied using heterozygous F508del DNA. After amplification, the effect of cooling rate (amplicon annealing from 85° C. to 61° C.) was studied by cooling at 20, 5, 2, 1, 0.5, 0.1, or 0.05° C./sec with melting at 0.2° C./sec. The heating rate (amplicon melting) was studied by cooling at 20° C./sec and melting at 0.05, 0.1, 0.2, or 0.4° C./sec. The effect of cations (Mg++ concentration) was studied by adjusting the concentration of the 44 bp amplicon with MgCl$_2$ to either 1, 2, 3, 4 or 5 mM, keeping all other concentrations constant (amplicon, buffer, etc.). The cooling rate was set at 20° C./s and the heating rate 0.1° C./s.

HTR2A Single Nucleotide Polymorphism

Each primer set surrounded a common polymorphism (T102C) within exon 1 of the HTR2A gene (Lipsky, R. H., et al., Clin. Chem. 47:635-644, 2001). A 115 base-pair fragment was amplified with the forward primer CACCAGGCTCTA-CAGTAATG (SEQ ID NO:5) and reverse primer TGAGAG-GCACCCTTCACAG (SEQ ID NO:6). In addition, 152 and 304 base-pair fragments were amplified with forward primer GCTCAACTACGAACTCCCT (SEQ ID NO:7) and reverse primers TGAGAGGCACCCTTCACAG (SEQ ID NO:8) and AGGAAATAGTTGGTGGCATTC (SEQ ID NO:9), respectively. The forward primers were 5'-labeled as an Oregon Green Simple-Probe (Idaho Technology). The polymorphism was 30 bases from the labeled end of the 115 bp product, and 67 bp away from the labeled ends of the 152 and 304 bp products. The 115 and 152 bp amplifications were cycled 40 times between 95° C., 60° C. with a 2 sec hold and 74° C. with a 10 sec hold. The 304 base-pair amplification was cycled 40 times between 95° C. and 70° C. with a 20 sec hold at 70° C. For all amplicons, a final melting curve was acquired on the LightCycler by heating to 95° C., cooling to 55° C. and then collecting fluorescence continuously at a ramp rate of 0.2° C./sec to 95° C.

Beta Globin Mutations (Hb S, C, and E).

PCR was performed in 100 mM 2-amino-2-methyl-1,3-propanediol, pH 8.8 with Taq polymerase (Roche) instead of in 50 mM Tris with KlenTaq. A 113 base pair fragment of the beta globin gene was amplified with primers TGCACCT-GACTCCT (SEQ ID NO:10) and CCTGTCTTGTAAC-CTTG (SEQ ID NO:11). The first primer was 5'-labeled as an Oregon Green Simple-Probe (Idaho Technology). The primers flank three single nucleotide polymorphisms, HbC (G16A); HbS, (A17T); and HbE (G76A).

After an initial denaturation for 10 seconds at 95° C. the samples were cycled 45 times with the following protocol: 95° C. with no hold, 51° C. with a 6 s hold, and a 1° C./sec ramp to 72° C. with no hold. LightCycler melting curves were acquired by heating to 95° C., cooling to 60° C. and then collecting fluorescence continuously at a ramp rate of 0.2° C./sec to 95° C. In some instances, a high resolution melting curve was obtained.

Indicator Primer System.

An indicator primer system was used for longer amplicon lengths at the CFTR locus. In addition to the sequence variants listed above, the polymorphism I506V was studied. In this indicator primer system, the locus-specific labeled primer was replaced with an unlabeled primer with a 5' tail. The 5' tail is homologous to the third labeled indicator primer that is also included in the reaction, but is not locus specific. Different loci can be studied with the same labeled primer by merely adding a homologous, unlabeled 5'-tail to one of the locus-specific primers (Nuovo, G. J., et al., J. Histochem. Cytochem. 47:273-279, 1999). A 243 base-pair fragment was amplified with the primers AGAATATACACTTCTGCTTAG (SEQ ID NO:12) (0.5 uM) and GCTGCACGCTGAGGTTCATCATAGGAAACACCA (SEQ ID NO:13) (0.05 uM). The underlined sequence is a target-independent tail, homologous to the indicator primer (Oregon Green)-GGGCTGCACGCTGAGGT (SEQ ID NO:14) (0.5 uM). PCR was performed by cycling 50 times between 95° C. and 65° C. (20 sec) and a high resolution melting curve was obtained.

Heteroduplex Detection Sensitivity Study (I506V).

The sensitivity of heteroduplex detection was studied by diluting heterozygous I506V DNA into wild type DNA. Heterozygous I506V DNA was mixed with wild type DNA in the proportions (wt:het), 0:1, 1:1, 4:1, 9:1, 19:1, 49:1, and 99:1. The 243 bp fragment was amplified and melted as indicated above.

Apo E Sequence Variants.

A 181 base-pair fragment of the apolipoprotein E gene was amplified with 2 mM MgCl$_2$ and primers GCGCGGACATG-GAGGAC (SEQ ID NO:15) and CGACGTGGCAGACGACCGGCCTGGTACACTGC (SEQ ID NO:16). The underlined sequence is a target independent tail that allows use of an indicator primer (BODIPY-FL)-CCCGACGTGGCAGACGA (SEQ ID NO:17) included at 0.25 uM in the amplification mixture. The primers surrounded 2 common polymorphisms, a T to C base change that converts the e3 genotype to the e4 genotype, and a C to T base change that converts the e3 genotype to the e2 genotype. After an initial denaturation for 1 min at 98° C., the samples were cycled 50 times between 98° C. (2 sec) and 70° C. (10 sec) with a ramping rate of 2° C./sec between 70 and 78° C. A high resolution melting curve was obtained.

Multi-Allele Detection Using Two Labeled Primers, Each with a Different Fluorophore.

A 181 base-pair fragment of the apolipoprotein E gene is amplified with 2 mM MgCl$_2$ and primers (Texas Red)-GCGCGGACATGGAGGAC (SEQ ID NO:18) and (BO-DIPY-FL)-CCGGCCTGGTACACTGC (SEQ ID NO:19). The primers surround 2 common polymorphisms, a T to C base change that converts the e3 genotype to the e4 genotype, and a C to T base change that converts the e3 genotype to the e2 genotype. After an initial denaturation for 1 min at 98° C., the samples are cycled 50 times between 98° C. (2 sec) and 70° C. (10 see) with a ramping rate of 2° C./sec between 70 and 78° C. High resolution melting data is analyzed.

Multi-Allele Detection Using One Labeled Primer and a GC Clamp on the Other Unlabeled Primer.

A 181 base-pair fragment of the apolipoprotein E gene is amplified with 2 mM MgCl$_2$ and primers (GC)n-GCGCG-GACATGGAGGAC (SEQ ID NO:20) and (BODIPY-FL)-CCGGCCTGGTACACTGC (SEQ ID NO:21) where n is chosen from 3 to 30. It is only necessary to stabilize the unlabeled end of the amplicon enough so that it melts in one transition. The primers surround 2 common polymorphisms, a T to C base change that converts the e3 genotype to the e4 genotype, and a C to T base change that converts the e3 genotype to the e2 genotype. After an initial denaturation for 1 min at 98° C., the samples are cycled 50 times between 98° C. (2 sec) and 70° C. (10 sec) with a ramping rate of 2° C./sec between 70 and 78° C. High resolution melting data is analyzed.

Haplotyping with Labeled Primers.

Different haplotypes can be distinguished if all the sequence variation that defines the haplotype is included in the melting domain of one labeled primer. When haplotyping is desired, in one embodiment a GC clamp is used with a single labeled primer to create one domain across the haplotype region. Since each haplotype is a unique sequence, most haplotypes will be distinguishable by their homoduplex melting curves. If 2 different haplotypes are present in a sample, 2 homoduplex products and 2 heteroduplex products define the melting curve. For example, amplification of HLA loci usually results in amplification of heterozygous products. Different genotypes will give different melting curves, allowing HLA typing.

Genotyping Highly Polymorphic Sequences.

In the case of infectious disease identification, amplified sequences are often highly polymorphic. For example, the DNA that codes for ribosomal RNA is highly variable and can be used for bacterial typing. Similarly, many viruses are highly polymorphic. For example, there are many types of human papilloma virus (HPV), different genotypes of hepatitis C virus (HCV), and different strains of human immunodeficiency virus (HIV). Determining the different types and strains is important for the prognosis and therapy of infection. Finding areas of consensus for primers can be difficult.

In one embodiment, all available sequences representing the groups that need to be differentiated are first aligned. Primers are selected and labeled so that allele specific amplification divides the groups into categories, each category corresponding to a different primer color. The target is amplified by PCR and a high resolution melting curve obtained. In an illustrated embodiment, because of the general lack of heterozygotes, slower temperature transitions may be used. In one illustrated embodiment, melting curve analysis is performed upon the conclusion of amplification, without a separate rapid cooling phase.

Data Analysis.

LightCycler and high resolution melting data were analyzed with either LightCycler software or custom software written in LabView. The data presented in FIGS. 1-4 were analyzed with standard LightCycler software. The data presented in FIGS. 5-14 used custom software with the following characteristics. Fluorescence vs temperature plots were normalized between 0 and 100 by first defining linear baselines before and after the melting transition for each sample. For each acquisition, the percent normalized fluorescence was calculated as the percent sample fluorescence between the baselines. In some cases, Savitsky-Golay filtering was used with a second degree polynomial and a data window including all points within a 1 degree interval (Wittwer C. T., et al., Real-Time PCR, in Diagnostic Molecular Microbiology: Principles and Applications. D Persing, et al., eds., ASM Press, in press, 2002). Derivative melting curve plots were calculated from the Savitsky-Golay polynomials at each point.

Results

Figure 1A:
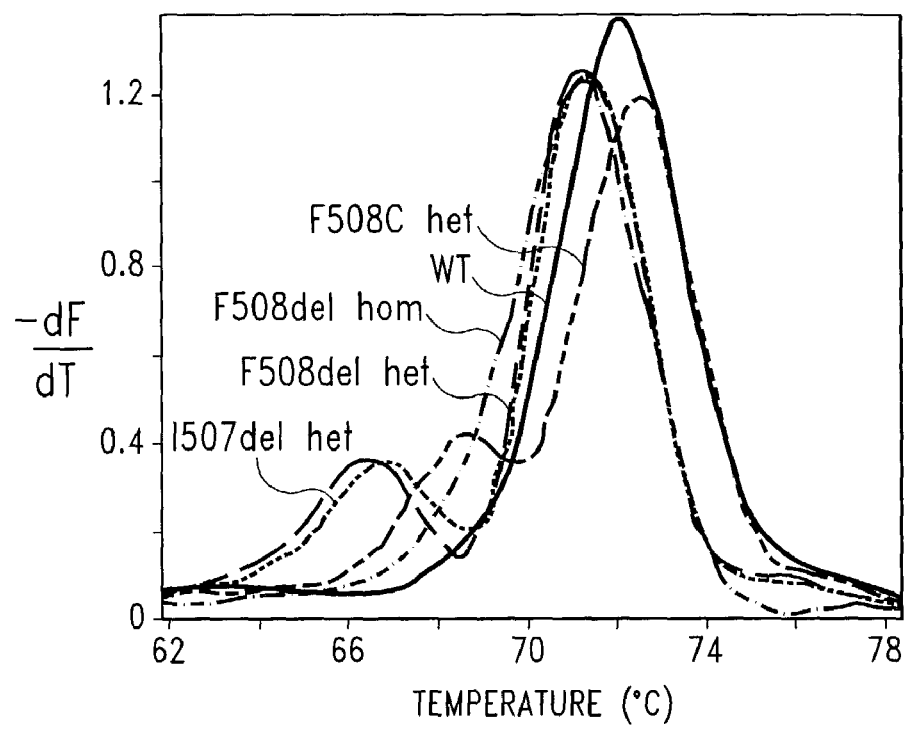
FIGS. 1A-B show genotyping of the cystic fibrosis transmembrane conductance regulator (CFTR) with a labeled primer (FIG. 1A) or SYBR Green I (FIG. 1B) on the LightCycler.
Figure 1B:
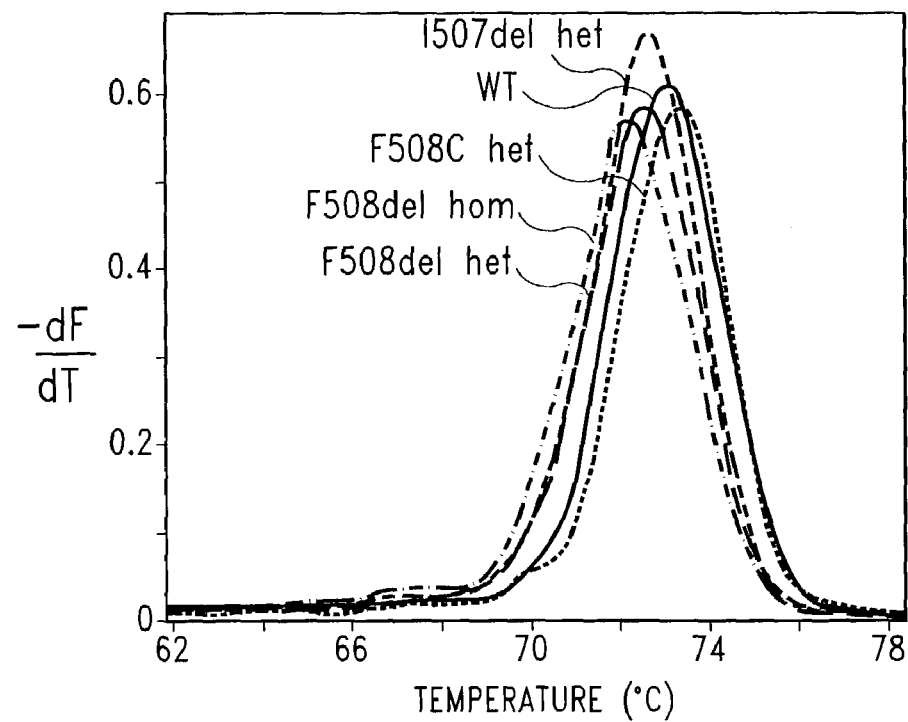

Initial conditions for optimal heteroduplex formation and melting with labeled primers were studied using a 44 bp fragment of the CFTR gene. With such a short amplicon, heteroduplexes melt as a distinct peak on derivative melting curve plots (FIGS. 1A-B). As expected, the heterozygotes with 3 bp deleted (F508del and I507del) result in heteroduplex peaks that are more destabilized than a single base change (F508C). The main F508C peak is actually higher melting than wild type, reflecting the greater stability of the T to G transversion (Gundry C. N., et al., Genetic Testing, 3:365-370, 1999). The heterozygote peaks for F508del and I507del are slightly offset. When SYBR Green I is included in the PCR with unlabeled primers, no distinct heterozygote peaks are observed under the same conditions.

Heteroduplex dependence on the cooling rate prior to melting indicates that rapid cooling is important for significant heteroduplex formation (FIGS. 2A-B), particularly with smaller amplicons. With a 44 bp amplicon, heteroduplexes are not observed when the cooling rate is 0.1° C./s or less. Heteroduplex formation appears to plateau at rates above 5° C./s. However, there is little difference in sample temperature transition rates when the LightCycler is programmed to cool at 5° C./s and 20° C./s, suggesting that heteroduplex formation may continue to increase at rates above 5° C./s. Indeed, the greatest amount of heteroduplex formation occurs when capillary samples are placed in boiling water and immediately quenched in ice water (data not shown).

Figure 3A:
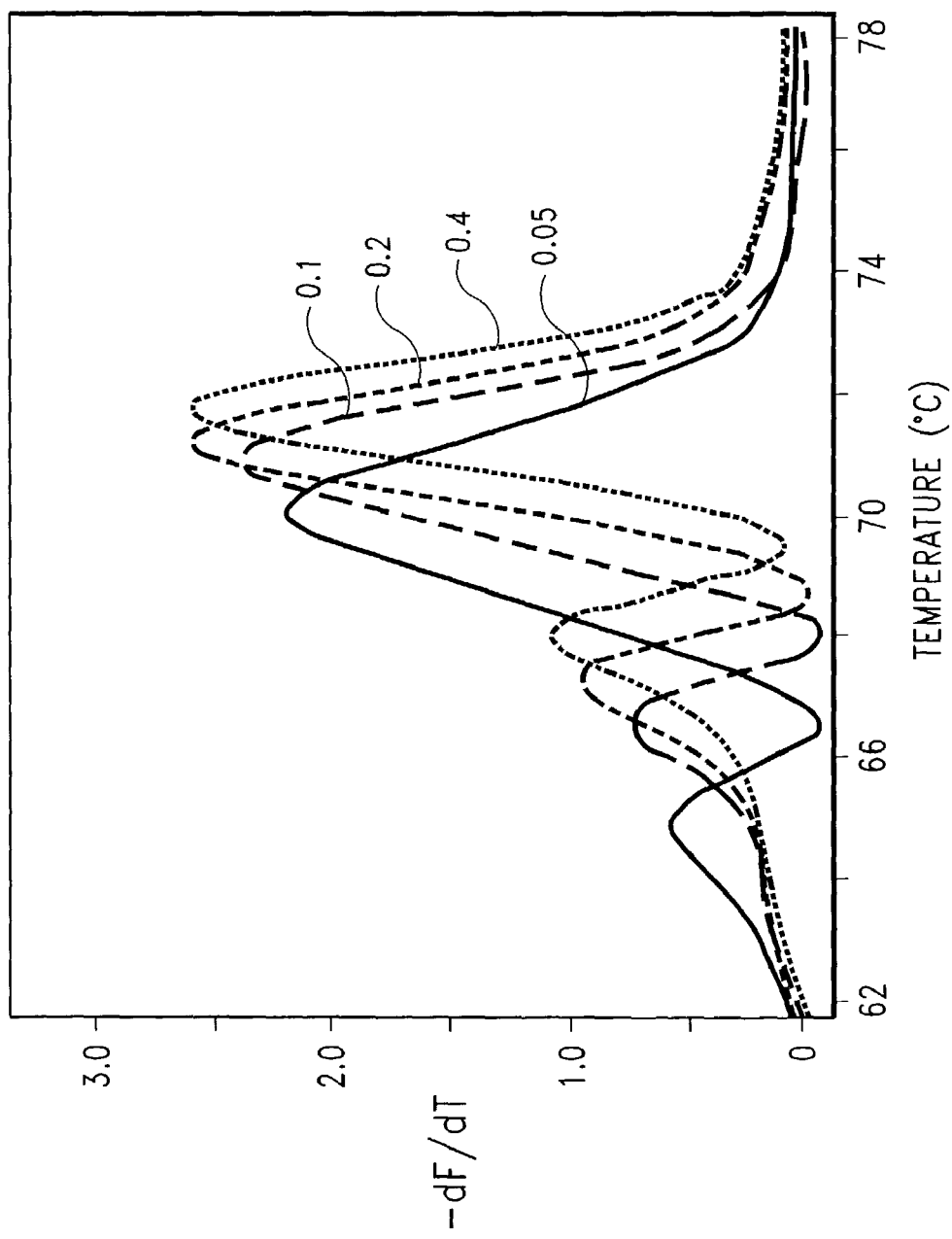
FIG. 3A illustrates that the observation of heteroduplexes is greater with rapid heating. Heterozygous F508del DNA was PCR amplified with one labeled primer. The samples were denatured, cooled, and heteroduplexes were observed during melting at different rates on the LightCycler.
Figure 3B:
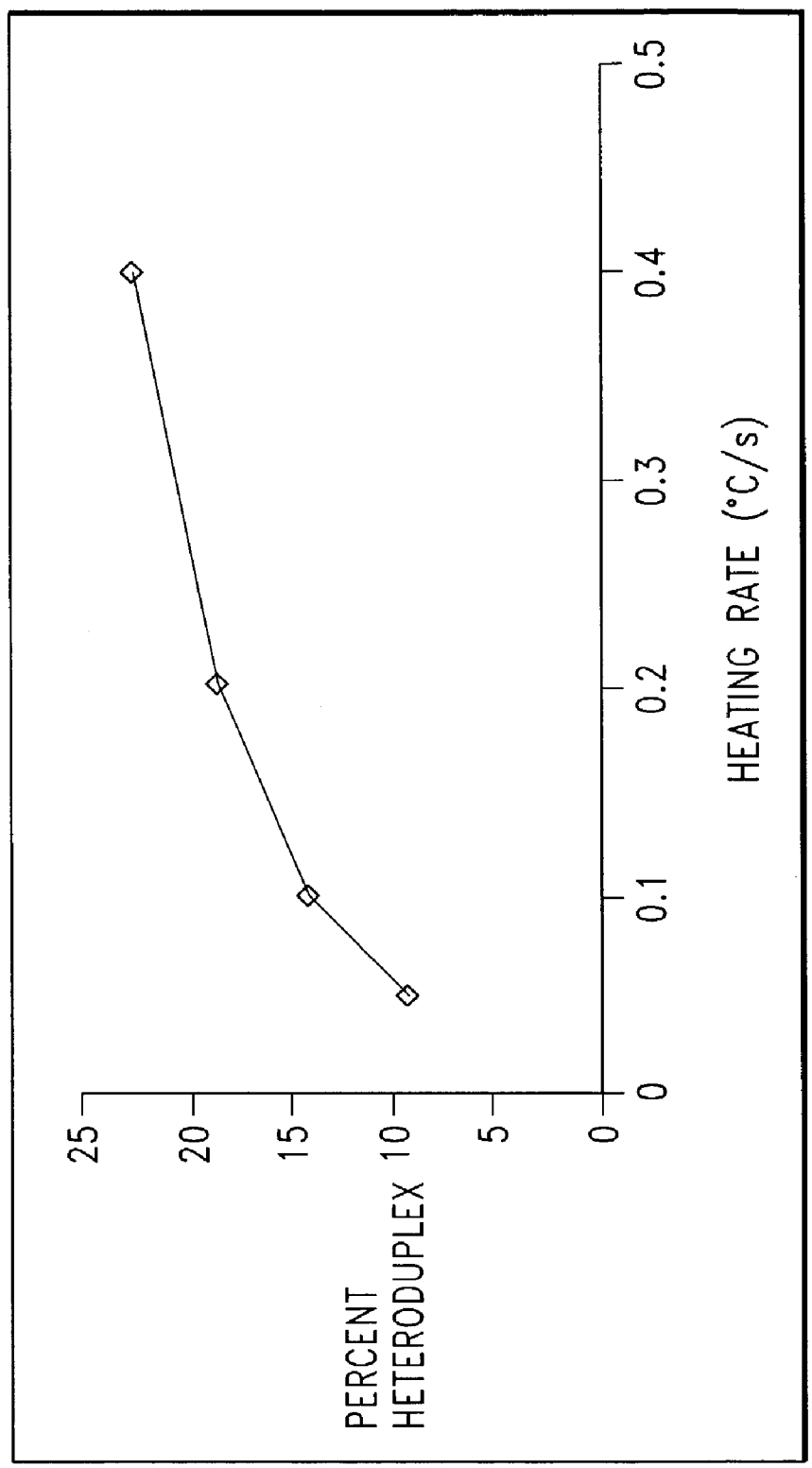
FIG. 3B diagrams the effect of heating rate (° C./s) on heteroduplex formation.
Figure 4A:
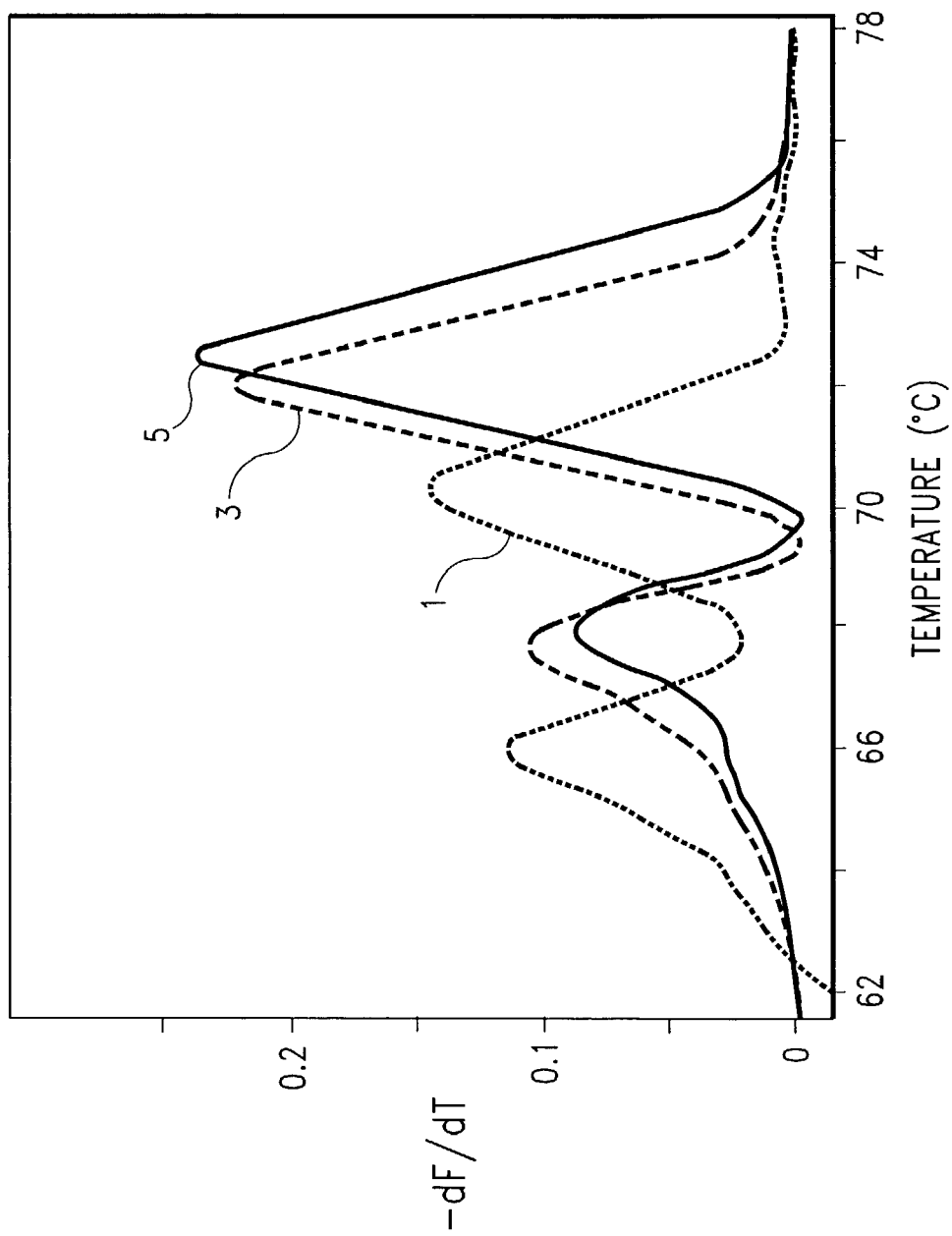
FIG. 4A shows formation of heteroduplexes at various Mg++ concentrations. Heterozygous F508del DNA was PCR amplified with one labeled primer. The Mg++ concentration was adjusted after amplification and heteroduplexes were observed during melting on the LightCycler.
Figure 4B:
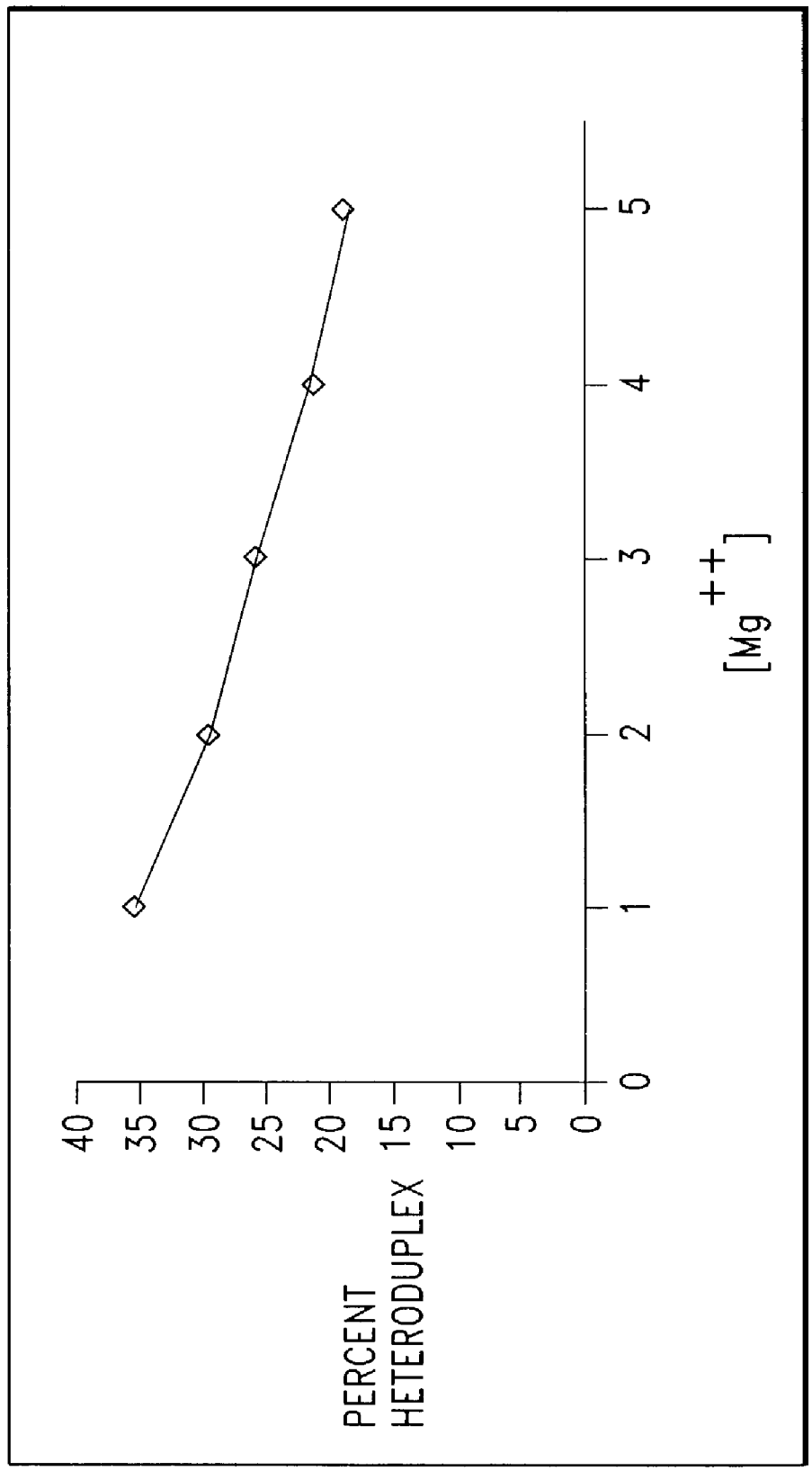
FIG. 4B diagrams the effect of magnesium concentration (mM) on heteroduplex formation.

With smaller amplicons, heteroduplexes are more apparent during melting at higher temperature transition rates (FIGS. 3A-B). The apparent Tm also shifts to higher temperatures with higher rates as the melting process deviates more from equilibrium (Gundry C. N., et al., Genetic Testing, 3:365-370, 1999). High transition rates may also limit the number of fluorescent acquisitions that can be taken per temperature interval.

More recent work has indicated that larger amplicons are less dependent on heating and cooling rate than are smaller amplicons. For example, with an amplicon of 100 bp the effect of heating and cooling rates is small, and with an amplicon of 200 bp the results appear about the same irrespective of the heating and cooling rate used. Additionally, it is understood that melting and reannealing prior to melting curve analysis is not required for every application. As used herein, melting and reannealing is used for detection of heteroduplexes to mix up the strands, often subsequent to the extension phase of amplification. Melting and reannealing is not needed in certain applications, particularly when only homoduplexes are present, as with various micro-organisms and viruses. Also, it is preferred to omit the melting and reannealing step when working with target sequences comprising short tandem repeats (STRs) and variable number tandem repeats (VNTRs). Illustratively, if VNTRs are denatured after extension, not only will heteroduplexes be produced, but the various repeated segments may not reanneal in the correct register, resulting in a very complex melting profile. However, if the VNTR target sequence is amplified without subsequent melting and reannealing, the homoduplexes that are present will melt in a relatively simple fashion, indicating the number of alleles present.

The relative percentage of heteroduplexes increases as the ionic strength decreases. The greatest effect is observed with Mg++ (FIGS. 4A-B), although K+ and Tris+ also show this effect (data not shown). As expected, the ionic strength also influences the Tm.

Figure 5A:
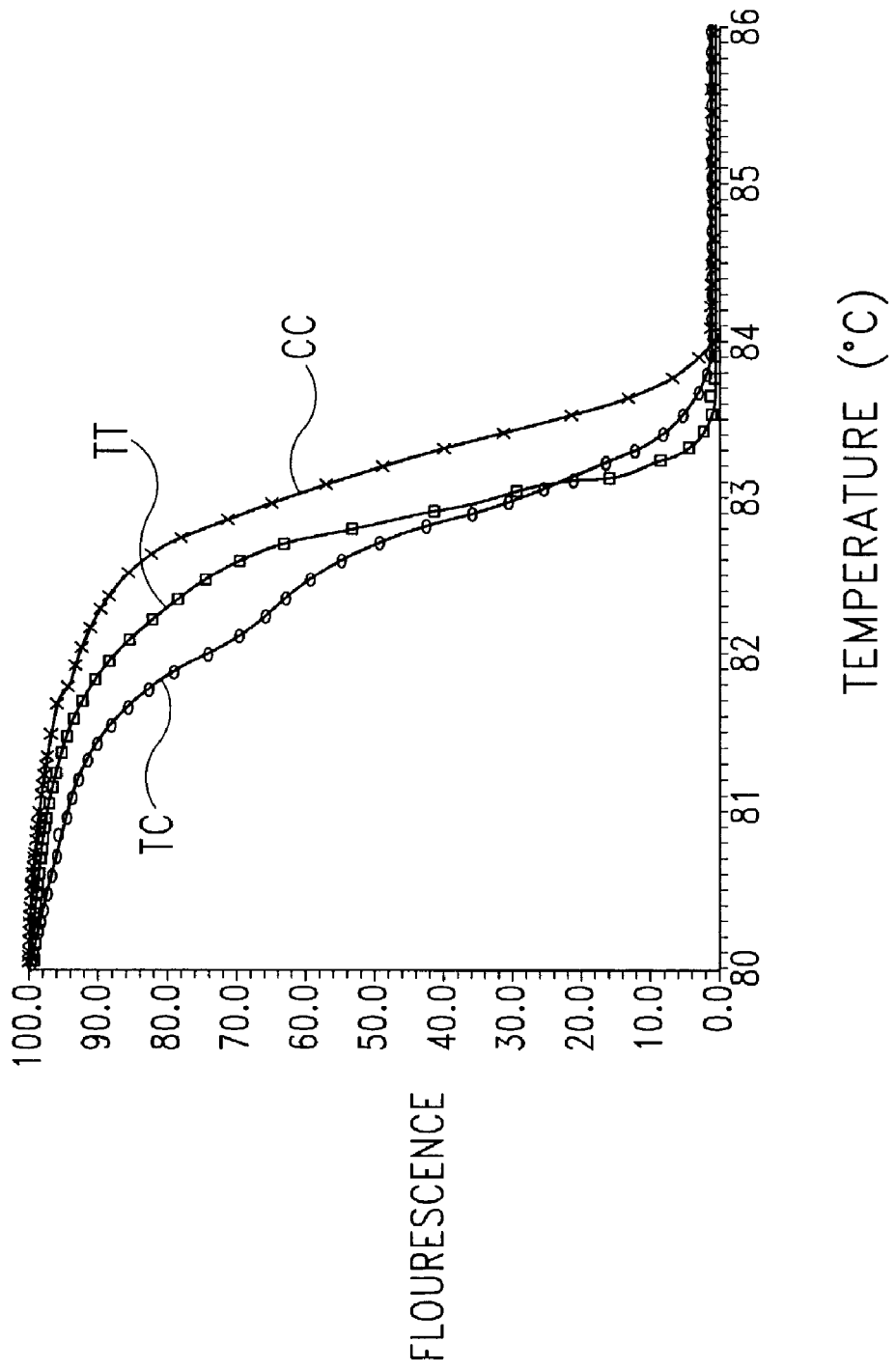
FIGS. 5A-C show genotyping of the T102C polymorphism of HTR2A with a labeled primer using 3 different amplicon lengths: 115 bp (FIG. 5A), 152 bp (FIG. 5B), and 304 bp (FIG. 5C). All three possible genotypes are shown for each product. The LightCycler was used for analysis.
Figure 5B:
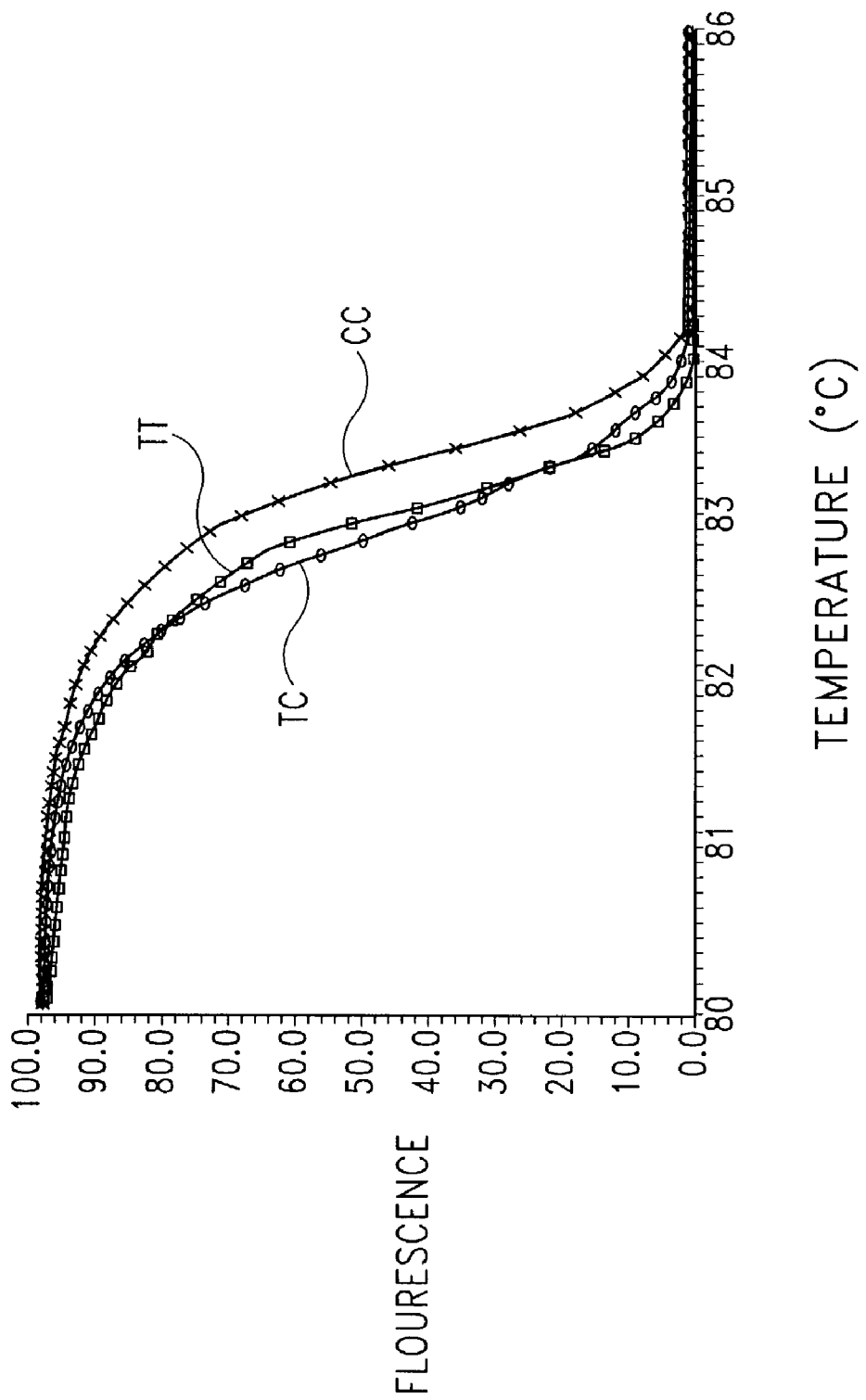
Figure 5C:
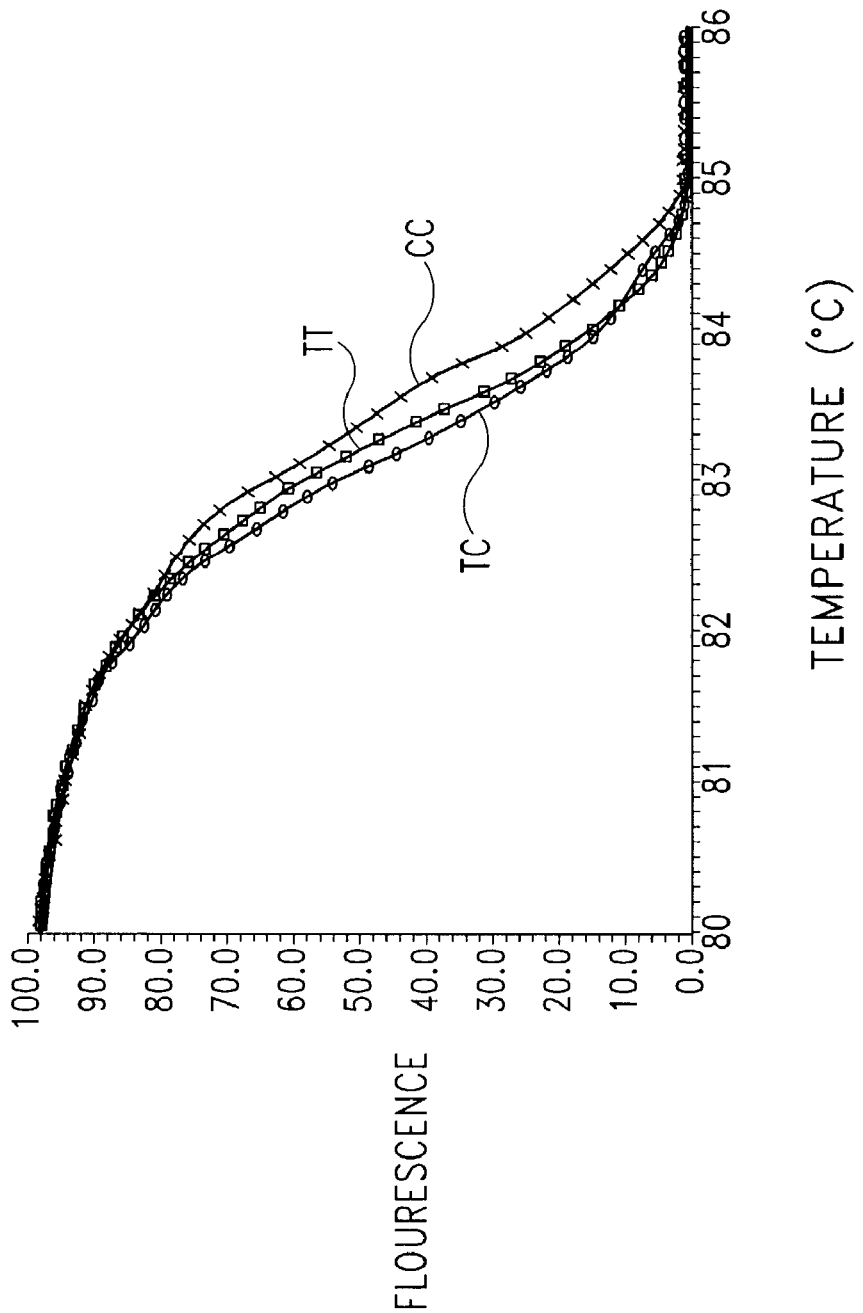

The effect of amplicon size on heteroduplex detection and genotyping is shown in FIGS. 5A-C. All three genotypes of an SNP in the HTR2A gene are analyzed, homozygous T, homozygous C and heterozygous at 3 different amplicon sizes. The homozygous C genotype is always more stable than the homozygous T genotype, allowing differentiation between homozygotes if appropriate controls are present. The heterozygote transition is always broader than the homozygote transitions, and the heterozygote curve crosses the less stable homozygote curve at high temperature. Although the difference between genotypes decreases as the amplicon size increases, all genotypes are still clearly differentiated at an amplicon size of 304 bp.

Figure 6:
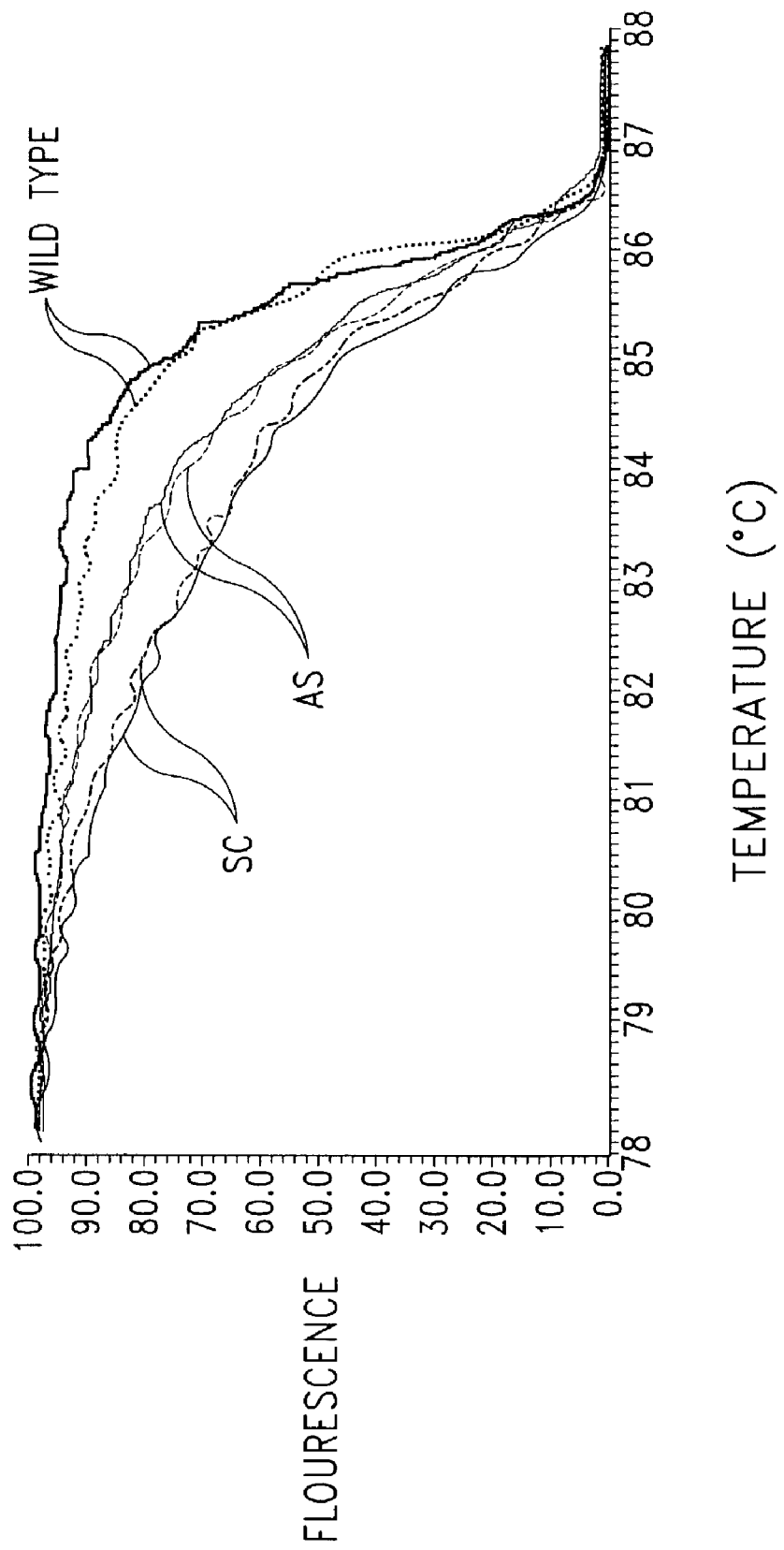
FIG. 6 shows genotyping of beta-globin mutations with labeled primers on the LightCycler. Wild type, heterozygous sickle cell (AS) and heterozygous SC were run in duplicate. Samples were run 4 samples at a time and data from multiple runs combined.
Figure 7A:
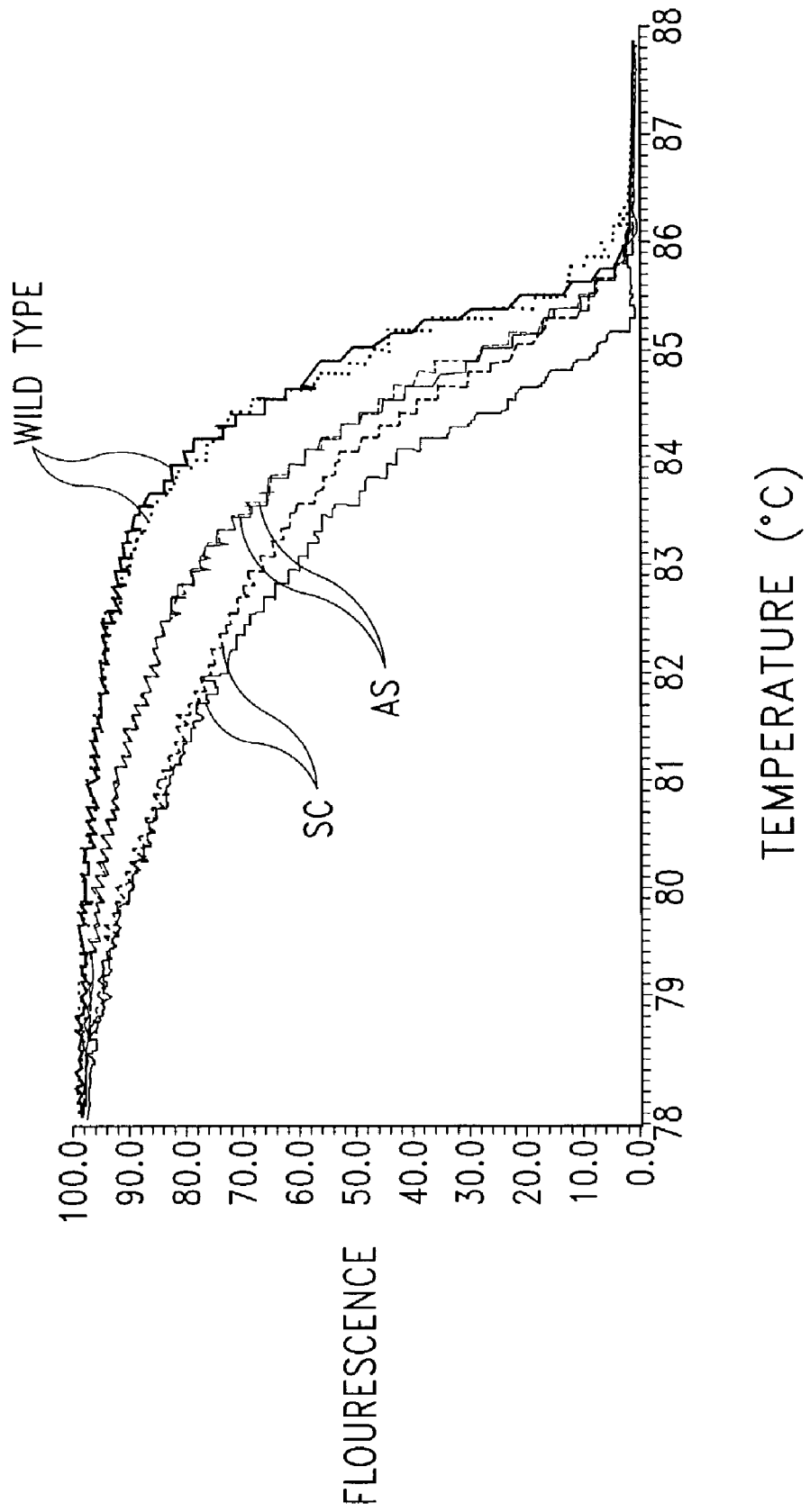
FIG. 7A shows genotyping of beta-globin mutations with labeled primers on the LightCycler. Wild type, heterozygous sickle cell (AS) and heterozygous SC were run in duplicate. Samples were run 1 sample at a time and data from multiple runs combined.
Figure 7B:
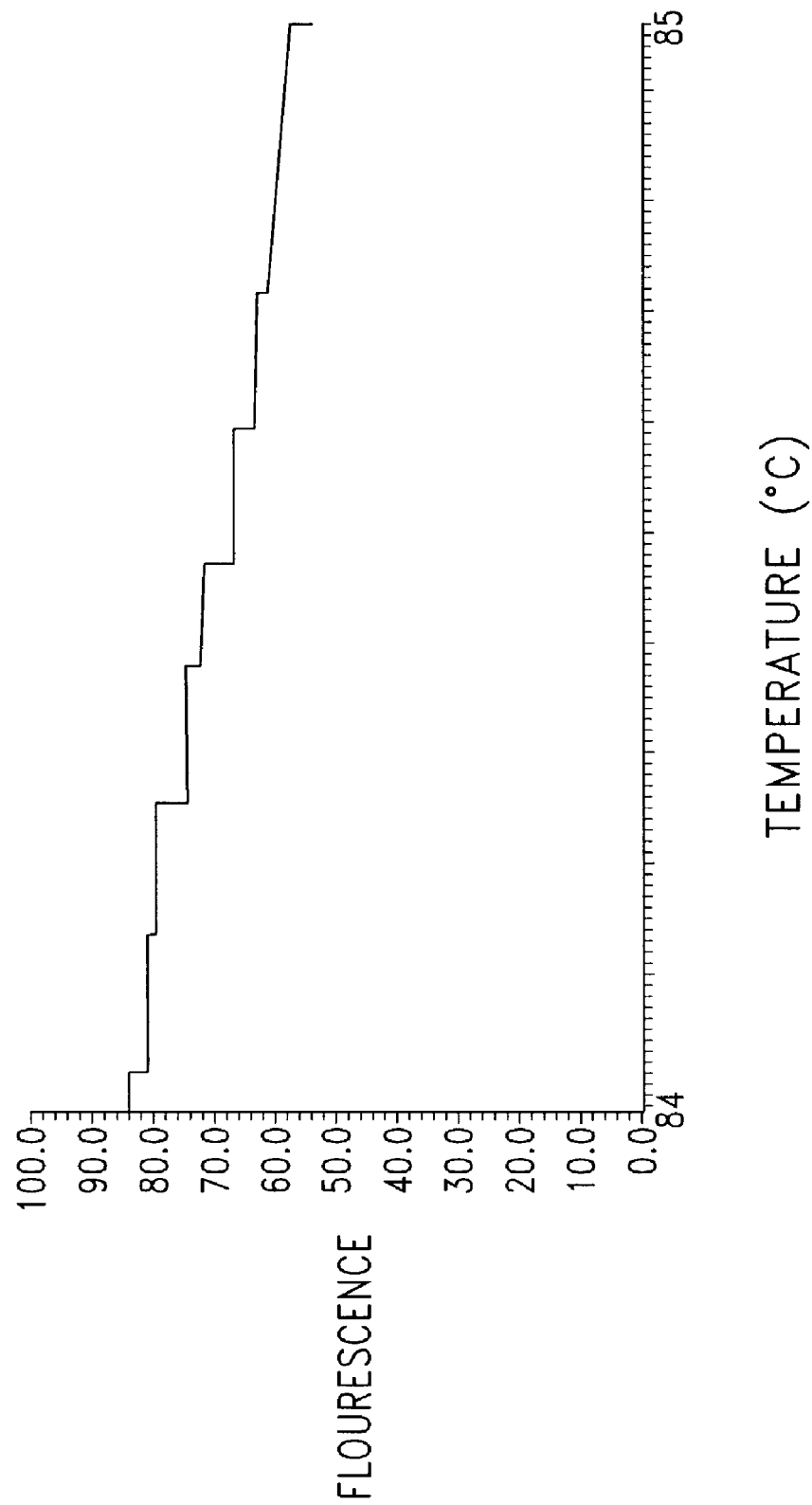
FIG. 7B shows a blowup of one of the wild type tracings from FIG. 7A between 84 and 85 degrees C., showing limited temperature resolution from 12-bit analog to digital conversion.
Figure 8:
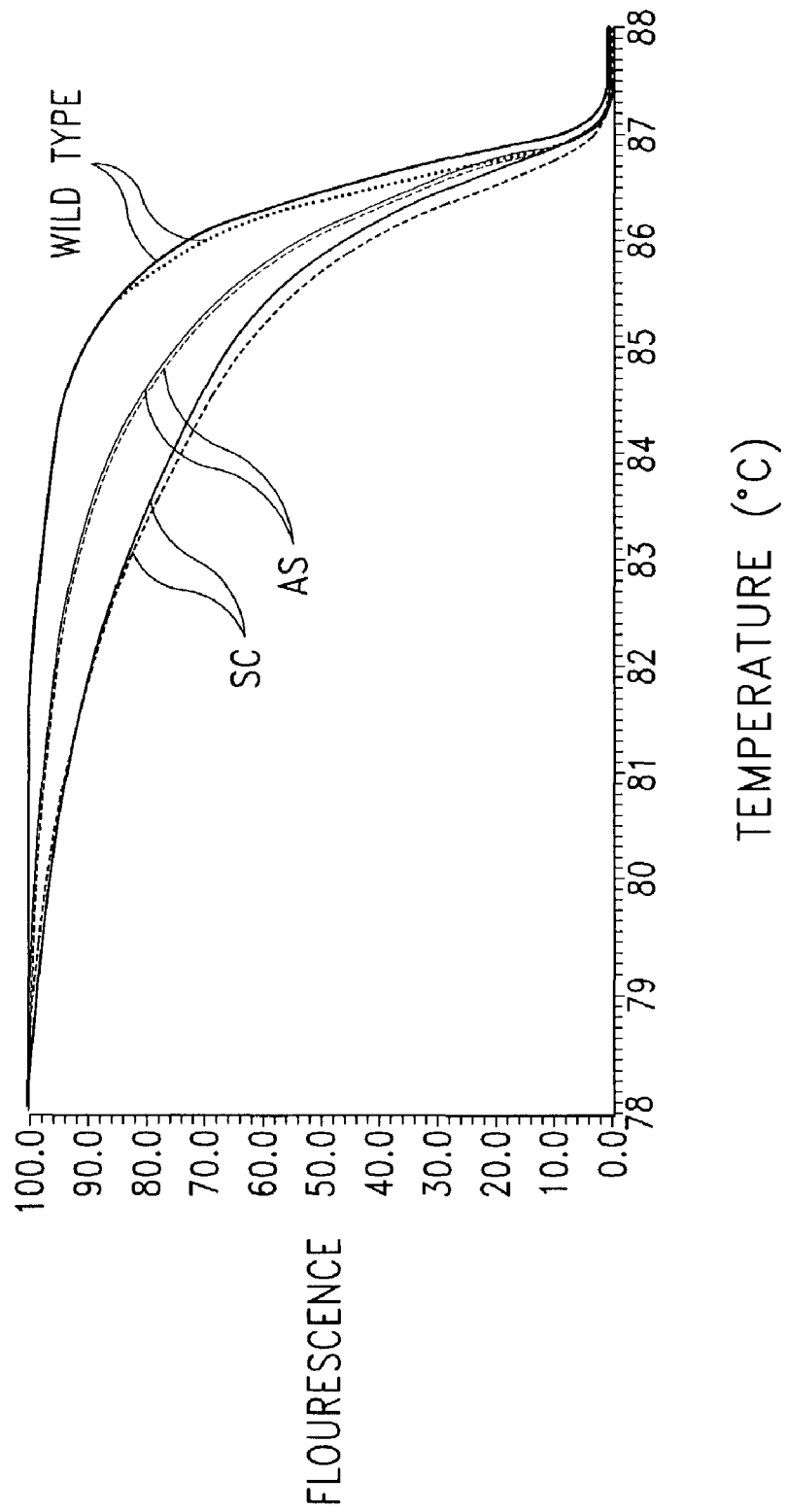
FIG. 8 shows genotyping of beta-globin mutations with labeled primers on a 16-bit high resolution instrument. Wild type, heterozygous sickle cell (AS) and heterozygous SC were run in duplicate. Samples were run 1 sample at a time and data from multiple runs combined.

The quality of the melting curves and the ability to distinguish different genotypes depends on the temperature resolution, fluorescence resolution and precision of the instrumentation used. FIG. 6 shows the normalized melting curves of 2 different DNA samples of each of 3 genotypes of beta-globin, wild type (AA), AS and SC. The 113 bp amplicons were melted 4 at a time at a rate of 0.2° C./s. Although all genotypes can be distinguished, significant noise in each trace is apparent. FIG. 7A shows the same samples run one at a time in the LightCycler. Although more acquisitions are taken, the apparent quality of the curves remains about the same. An analog to digital conversion limitation becomes apparent because the 12-bit temperature converter limits the resolution to 8-9 divisions per degree C. (FIG. 7B). Much better resolution can be obtained with 16-bit conversion of temperature and fluorescence (FIG. 8). The high-resolution instrument also ensures greater temperature homogeneity within the sample because the cylindrical capillary is completely surrounded by an aluminum cylinder. With present equipment, although only a single sample can be run at one time, a 0.3° C./s melting curve requires less than 3 min and 50-100 acquisitions per degree C. can be acquired.

Figure 9:
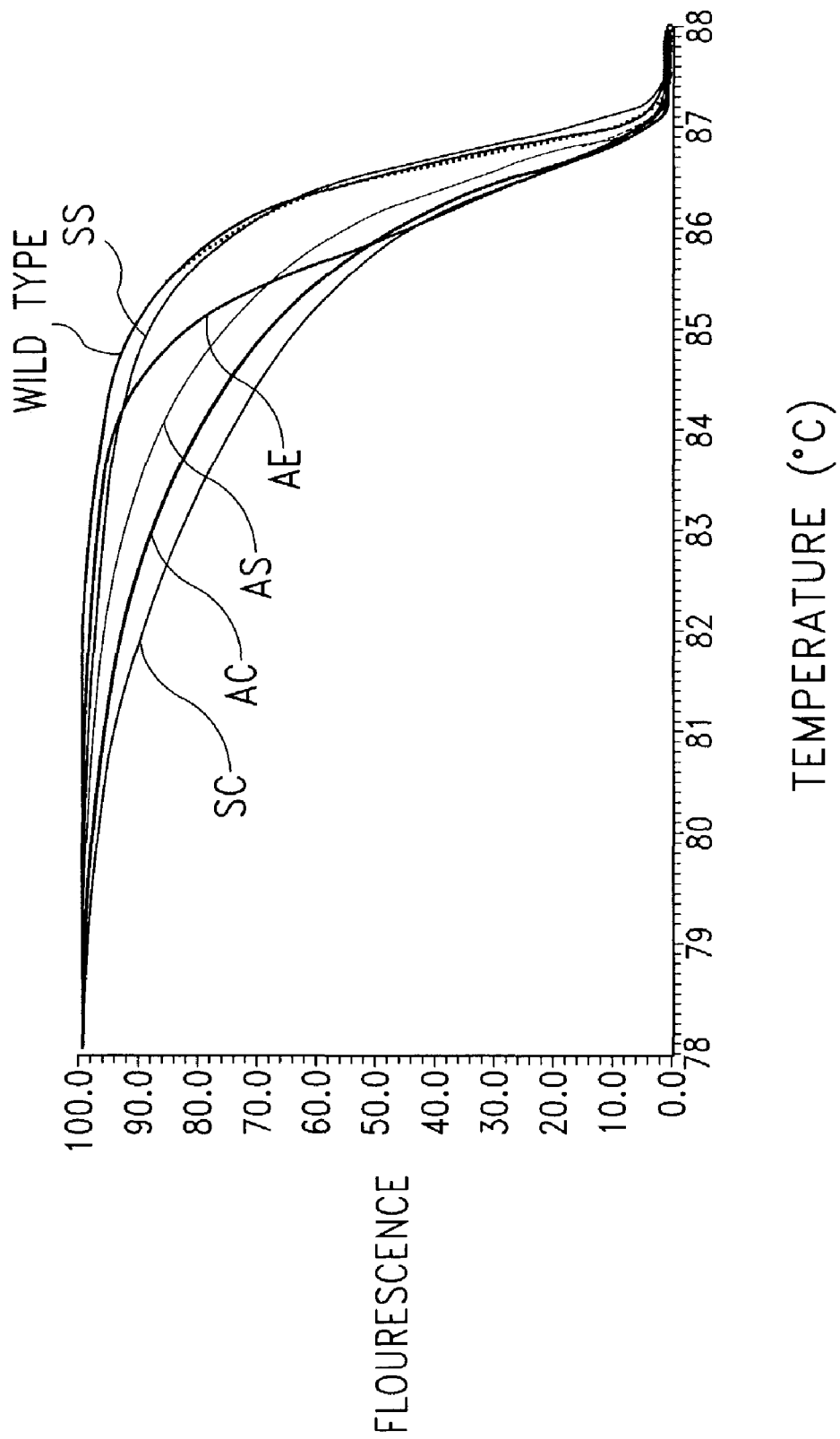
FIG. 9 shows genotyping of the 6 most common beta-globin genotypes with labeled primers on a 16-bit high resolution instrument. The wild type and SS tracings are nearly identical, while all heterozygous genotypes (AC, AE, AS and SC) trace unique paths of fluorescence over temperature.
Figure 10:
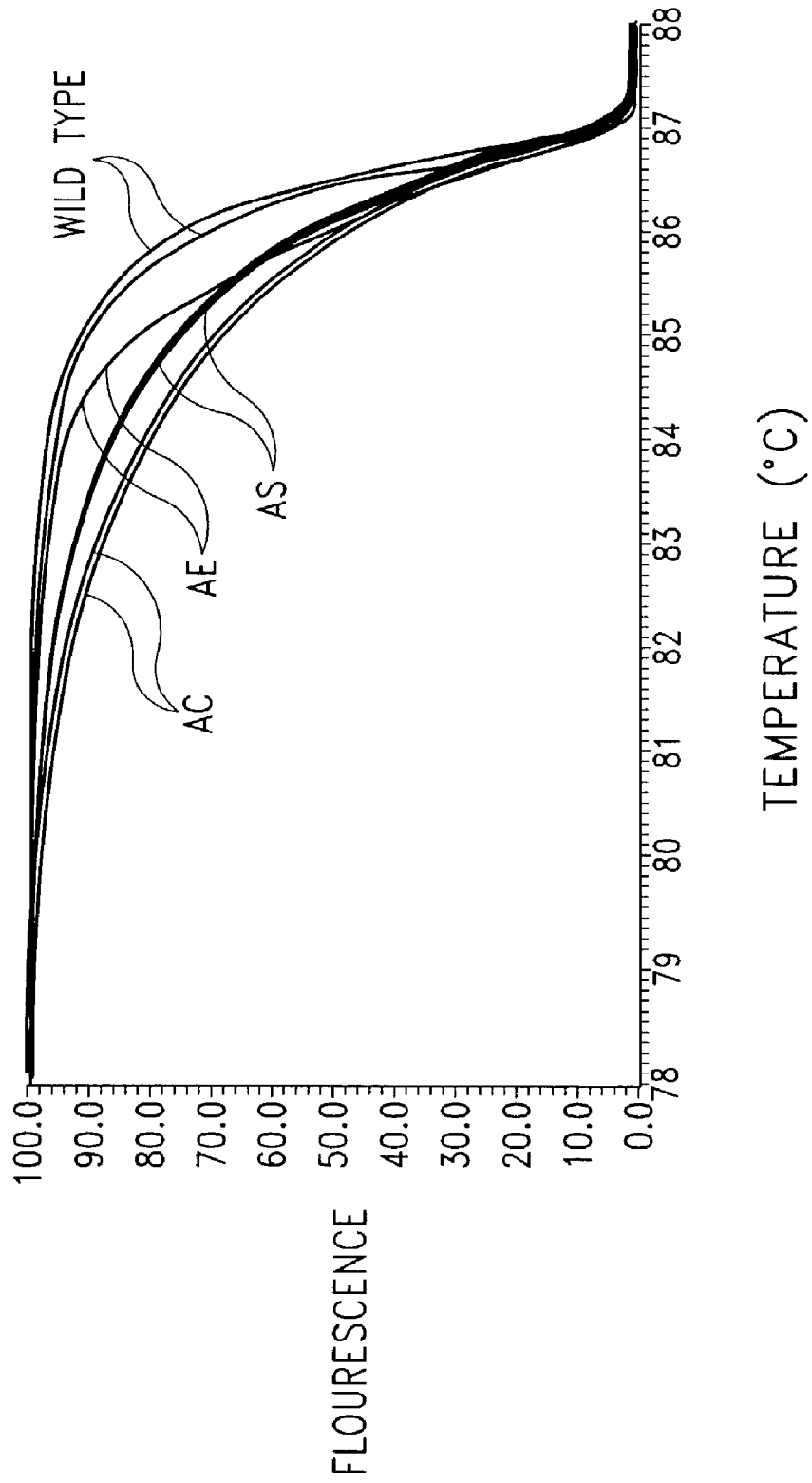
FIG. 10 shows differentiation of wild type and beta-globin heterozygotes by high resolution melting. Duplicates of wild type, AC, AE, and AS genotypes are shown.

The normalized melting curves of the 6 most common beta-globin genotypes are shown in FIG. 9. All 4 heterozygotes (AC, AE, AS, and SC) are clearly distinguished from the homozygotes, and all heterozygotes appear different from each other. Further evidence that the heterozygotes can be distinguished is shown in FIG. 10, where 2 DNA samples of each of the simple heterozygotes (AC, AE, and AS) are shown along with 2 AA (wild type) samples. Within a genotype, the tracings closely overlap.

Figure 11:
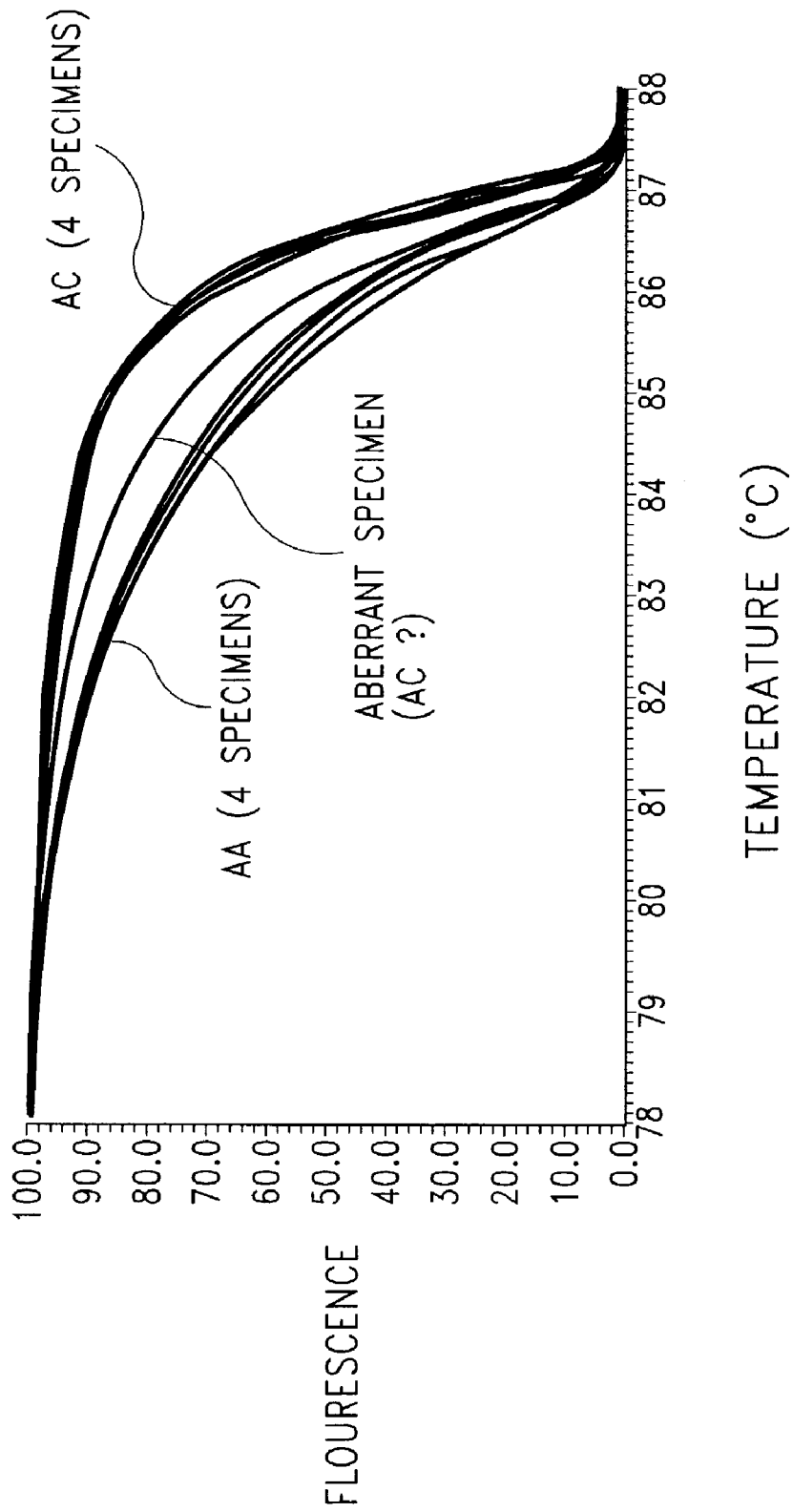
FIG. 11 shows identification of an aberrant AC heterozygote. Five different AC samples (typed by conventional adjacent hybridization probes) and 4 different wild type samples were analyzed by high resolution melting. The wild type and AC groups are clearly distinct, except for one AC sample with a tracing in between the wild type and AC groups. Sequencing of the aberrant sample revealed an AC genotype with an additional heterozygous base within one of the primer sequences.

When several AA and AC samples were melted, one aberrant AC sample ran between the AA and AC groups (FIG. 11). This AC sample was previously typed by hybridization probe melting curve analysis (Herrmann M., et al., Clin. Chem., 46:425-428, 2000). By sequencing the region, the G16A heterozygote found in AC individuals was confirmed, but sequencing also revealed an additional heterozygous position, located under the labeled primer TGCA(C/T)CT-GACTCCT. Apparently, partial allele specific amplification occurred, overproducing the AA amplicon and resulting in fewer heteroduplexes with a melting curve between the AA and AC groups. While it is difficult to distinguish the 2 homozygotes (AA and SS), as might be predicted from the A to T base change, the two homozygotes (AA and SS) were distinguishable using Oregon Green attached to a 5' terminal T residue, without Simple Probe chemistry (results not shown).

Figure 12:
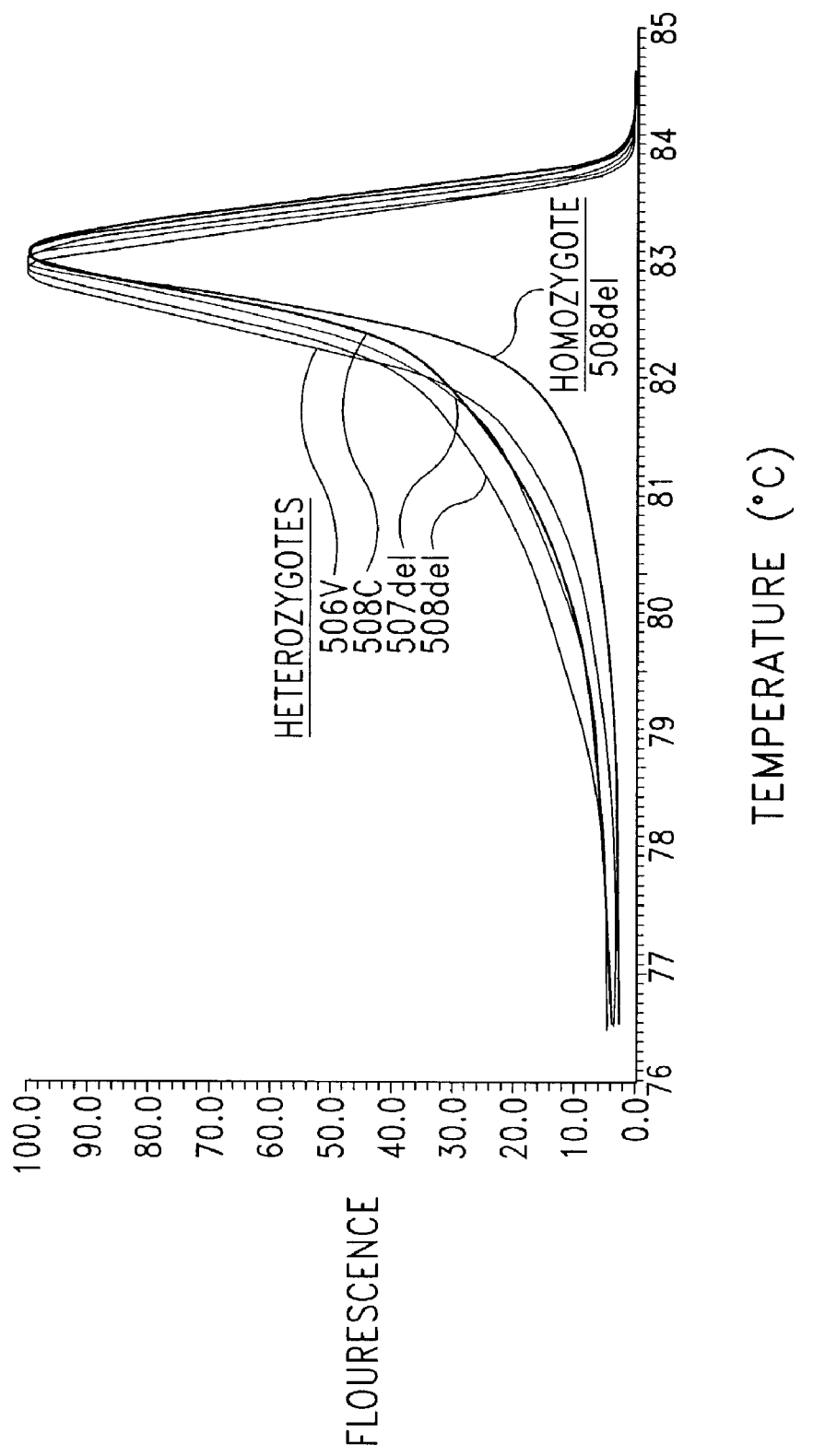
FIG. 12 shows genotyping with a labeled indicator primer. A 243 bp fragment of the CFTR gene was amplified in the presence of three primers: a labeled indicator primer, an unlabeled primer with a 5'-tail homologous to the indicator, and an additional reverse primer. Multiple rounds of PCR incorporate the sequence of the indicator into the final PCR product. Tracings of wild type DNA, two 3-base deletions (508del and 507del) and two single nucleotide polymorphisms (508C and 506V) are shown.
Figure 13A:
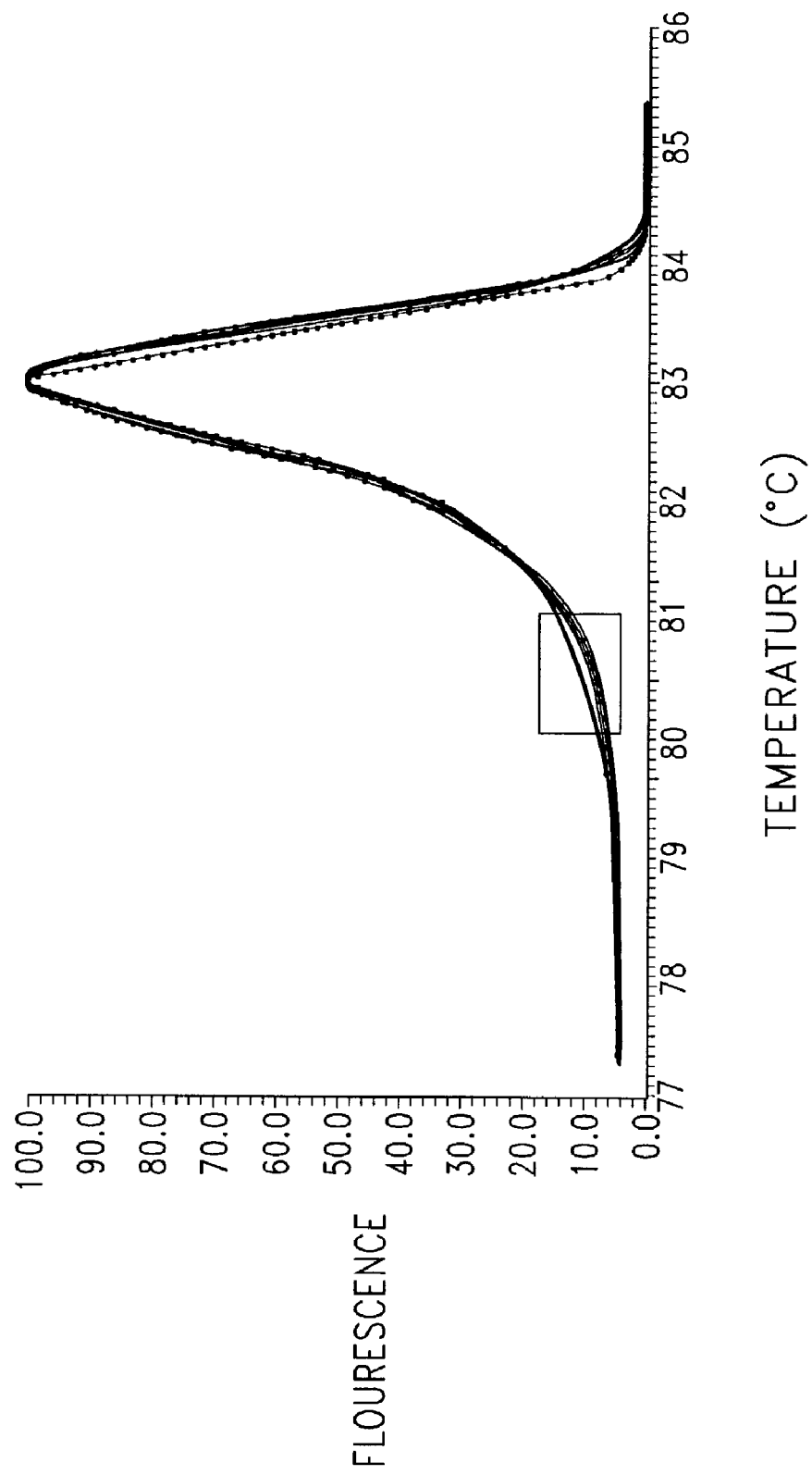
FIG. 13A shows detection sensitivity of 1506V DNA in wild type DNA using a 243 bp CFTR fragment and a labeled indicator primer. Relative allele concentrations varied from 50% (heterozygous DNA) to 0.5% (99:1).
Figure 13B:
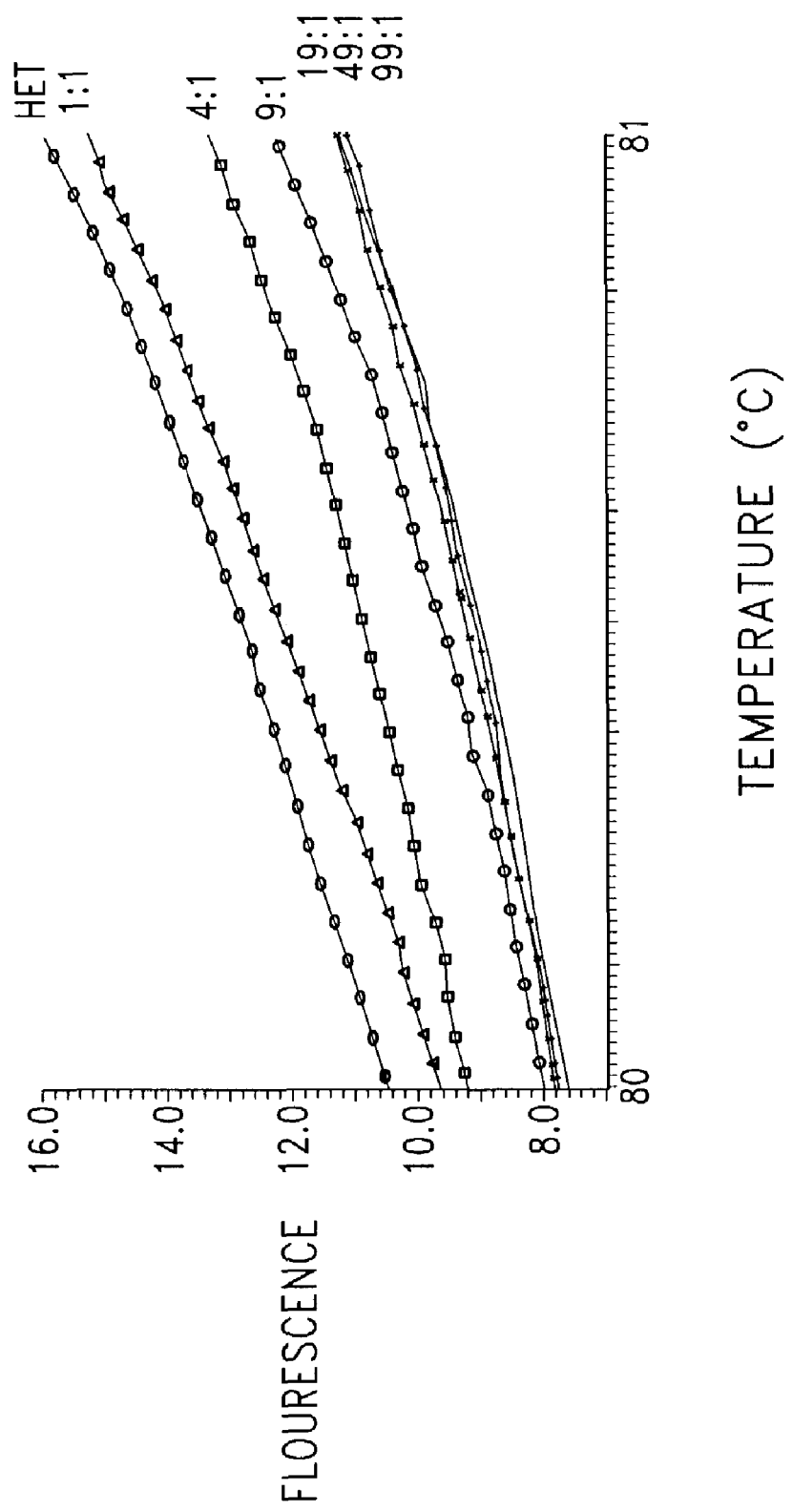
FIG. 13B shows magnification of FIG. 13A between 80 and 81 degrees C. Samples containing 5% of the less prevalent allele are clearly distinguished from higher dilutions.

FIG. 12 displays derivative melting curve plots of different genotypes within a 243 bp CFTR amplicon using an indicator primer. The low temperature shoulders are displayed on all 4 heteroduplexes, clearly distinguishing them from the homozygous sample. The detection sensitivity of I506V DNA diluted in wild type DNA is studied in the derivative melting curve plots of FIGS. 13A-B. The boxed area of FIG. 13A is blown up in FIG. 13B. The 9:1 sample (5% I506V DNA) is clearly separated from higher dilutions.

Figure 14:
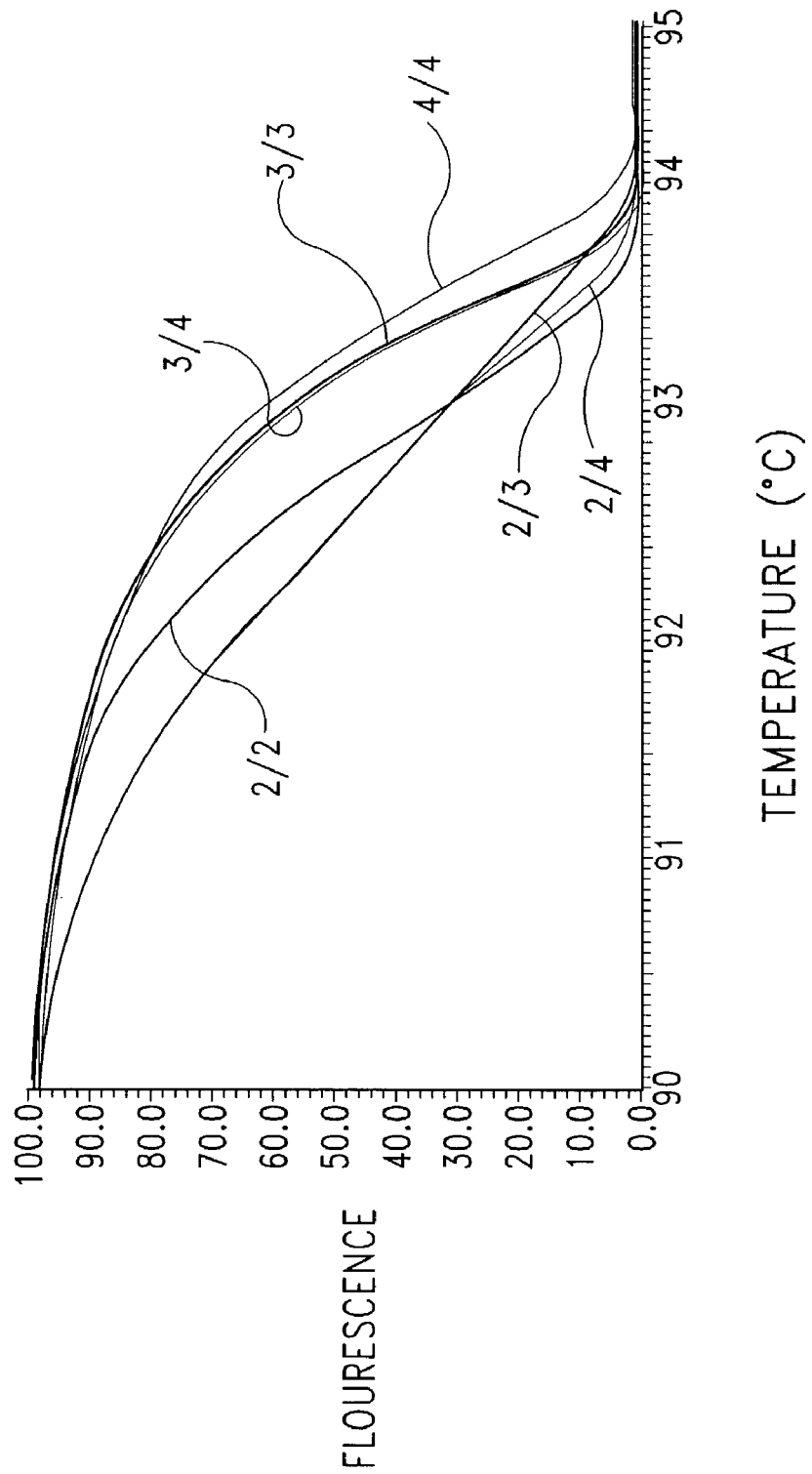
FIG. 14 shows ApoE genotyping using a labeled indicator primer and a 181 bp amplicon. All homozygotes (2/2, 3/3, and 4/4) are clearly distinguished, while the 3/4 heterozygote appears identical to the 3/3 homozygote, and the 2/4 heterozygote is very similar to the 2/3 heterozygote.

Normalized melting curves of the 6 common apo E genotypes are shown in FIG. 14, produced by melting a 181 bp amplicon that brackets 2 single nucleotide polymorphisms. An indicator primer was used. All homozygotes are distinguishable from each other by Tm in the order expected from the stability of the base changes. However, the 3/4 heterozygote is identical to the 3/3 homozygote, and the 2/3 heterozygote is nearly identical to the 2/4 heterozygote. That is, the apoE4 haplotype looks like the apoE3 haplotype when E4 is heterozygous.

When both primers are labeled, one with BODIPY-FL and one with Texas Red, both polymorphisms within the apoE amplicon can be detected. After application with temperature-dependent color compensation (Wittwer C. T., et al., Methods, 25:430-442, 2001), the e3/e4 polymorphism is detected in the Texas Red channel, and the e3/e2 polymorphism in the BODIPY-FL channel. Each labeled primer detects all polymorphisms within its melting domain.

Both polymorphisms in the apoE amplicon can be detected with one labeled primer if a GC-clamp is added to the opposite primer. Without a GC clamp, the e3/e4 polymorphism is missed when heterozygous. The e3/e4 heteroduplexes melt before the rest of the amplicon that includes the labeled primer (FIG. 14). As the length of the GC clamp increases, the e3/e4 locus is stabilized such that the entire amplicon melts in one domain. At even longer GC clamp lengths, the GC clamps melts after the rest of the amplicon. In this case as well, both polymorphisms can be detected.

For haplotype analysis, each haplotype contributes a unique homoduplex melting curve, and each binary combination of haplotypes produces 2 homoduplex products and 2 heteroduplex products. Because the amplification of different heterozygotes results in different melting curves (FIG. 10), genotyping by haplotype analysis is possible. The number of genotypes that can be distinguished depends on the resolution of the melting curve data.

Figure 15:
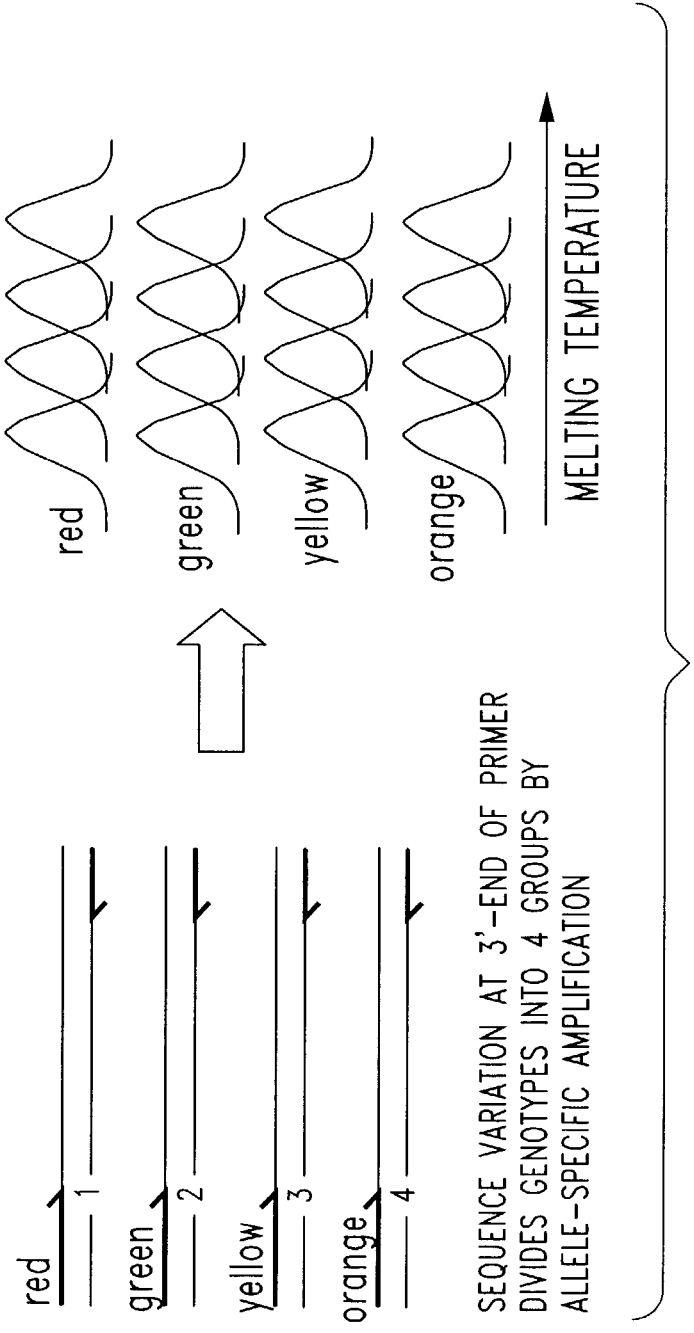
FIG. 15 shows a scheme for typing highly polymorphic sequences. Allele specific amplification is used to subdivide all possible genotypes into different colors using labeled primers. Then, high resolution melting analysis divides each color group into specific genotypes, depending on the Tm and melting profile of each genotype.

Highly polymorphic sequences can be difficult to genotype. One scheme for typing such sequences using labeled primers is shown in FIG. 15. Allele specific amplification with primers labeled with various dyes having different emission frequencies is used to divide the groups into categories. Depending on the degree of sequence variation, the amplicons can be chosen to be either long, if little variation is present, or short, if extensive variation is present. Within each color, products are classified by their melting temperature. Many different sequences can be distinguished, providing a simple, real time technique for complex genotyping tasks.

Although the invention has been described in detail with reference to certain preferred embodiments, variations and modifications exist within the scope and spirit of the invention as described and defined in the following features.

The invention claimed is:

1. A method for identifying a heterozygote in a nucleic acid sample, comprising
   a) amplifying the target nucleic acid in a nucleic acid amplification reaction mixture to generate an amplification product, the amplification reaction mixture comprising
      aa) a polymerase,
      ab) deoxynucleoside triphosphates or functional analogues,
      ac) at least a first primer and a second primer,
      the first primer being sufficiently complementary to the target nucleic acid to hybridize therewith and initiate template dependent synthesis by the polymerase,
      the second primer being sufficiently complementary to the complement of the target nucleic acid to hybridize therewith and initiate template dependent synthesis by the polymerase,
      characterized in that at least one primer is labeled with a fluorescent compound which is not in a FRET donor-acceptor relationship with any other fluorescent entity that may be present in the sample, the labeled primer being selected from the group consisting of
         i) the first primer,
         ii) the second primer, and
         iii) an indicator primer, the indicator primer being sufficiently complementary to hybridize to a DNA fragment that is amplified only if the first and second primers are used to initiate synthesis by the polymerase, the labeled primer configured to generate a full length complementary sequence,
   b) denaturing the amplification product into single strands and subsequently renaturing the single strands to form a double stranded product, said double stranded product comprising duplexes formed between an amplification extended labeled primer and a full length complementary sequence,
   c) subjecting the renatured amplification mixture containing the amplified target sequence to a double stranded DNA denaturing gradient and simultaneously monitoring fluorescence emission to generate a curve, and
   d) identifying the heterozygote by analyzing the shape of the curve generated from the melting of duplexes formed between the amplification extended labeled primer and the full length complementary sequence.

2. The method of claim 1, wherein the curve has a main melting transition, and the heterozygote is identified by a shoulder on a low temperature side of the main melting transition as compared to the same melting curve for a homozygote of the double stranded product.

3. The method of claim 2, wherein the curve has a broadening of the peak on the main melting transition.

4. The method of claim 2, wherein the heterozygote is identified from a different heterozygote due to the shape of said shoulder.

5. The method of claim 1, wherein a first allele is present at a concentration less than a concentration of a second allele.

6. The method of claim 5, wherein the sample contains no more than 10% of the first allele.

7. The method of claim 5, wherein the sample contains 5% of the first allele.

8. The method of claim 1, wherein the labeled primer is labeled at the 5'-end and the heterozygote has a sequence variation at least 30 bases from the fluorescent compound.

9. The method of claim 8, wherein the heterozygote has a sequence variation at least 67 bases from the fluorescent compound.

10. The method according to claim 1, wherein the sample has a magnesium concentration not greater than 3 mM.

11. A method for identifying a heterozygote in a nucleic acid sample, comprising
    a) amplifying the target nucleic acid in a nucleic acid amplification reaction mixture to generate an amplification product, the amplification reaction mixture comprising
       aa) a polymerase,
       ab) deoxynucleoside triphosphates or functional analogues,
       ac) at least a first primer and a second primer,
       the first primer being sufficiently complementary to the target nucleic acid to hybridize therewith and initiate template dependent synthesis by the polymerase,
       the second primer being sufficiently complementary to the complement of the target nucleic acid to hybridize therewith and initiate template dependent synthesis by the polymerase,
       ad) a fluorescent entity bound to the 5' terminus of the first or second primer,
    b) denaturing the amplification product into single strands and subsequently renaturing the single strands to form a double stranded product, said double stranded product comprising duplexes formed between an amplification extended labeled primer and a full length complementary sequence,
    c) subjecting the renatured amplification mixture containing the amplified target sequence to a double stranded DNA denaturing gradient and simultaneously monitoring fluorescence emission to generate a curve, and
    d) identifying the heterozygote by analyzing the shape of the curve, wherein the curve is generated from the melting of duplexes formed between the amplification extended labeled primer and the full length complementary sequence, and the curve has a main melting transition, wherein the heterozygote is identified by a shoulder on a low temperature side of the main melting transition as compared to the same melting curve for a homozygote of the double stranded product.

12. The method of claim 11, wherein the curve has a broadening of the peak on the main melting transition.

13. The method of claim 12, wherein the heterozygote is identified from a different heterozygote due to the shape of said shoulder.

14. The method of claim 11 wherein a first allele is present at a concentration less than a concentration of a second allele.

15. The method of claim 14, wherein the sample contains no more than 10% of the first allele.

16. The method of claim 15, wherein the sample contains no more than 5% of the first allele.

17. The method of claim 11, wherein the labeled primer is labeled at the 5'-end and the heterozygote has a sequence variation at least 30 bases from the fluorescent compound.

18. The method of claim 17, wherein the heterozygote has a sequence variation at least 67 bases from the fluorescent compound.

19. The method of claim 11, wherein the monitoring of fluorescence emission is performed with at least 16-bit data acquisition.

* * * * *

SEQUENCE LISTING

<160> NUMBER OF SEQ ID NOS: 21

<210> SEQ ID NO 1
<211> LENGTH: 15
<212> TYPE: DNA

-continued

```
<213> ORGANISM: artificial sequence
<220> FEATURE:
<223> OTHER INFORMATION: Synthetic primer

<400> SEQUENCE: 1
gctgcacgct gaggt                                                      15

<210> SEQ ID NO 2
<211> LENGTH: 18
<212> TYPE: DNA
<213> ORGANISM: artificial sequence
<220> FEATURE:
<223> OTHER INFORMATION: synthetic primer

<400> SEQUENCE: 2
caccattaaa gaaaatat                                                   18

<210> SEQ ID NO 3
<211> LENGTH: 20
<212> TYPE: DNA
<213> ORGANISM: Homo sapiens

<400> SEQUENCE: 3
ggcaccatta agaaaatat                                                  20

<210> SEQ ID NO 4
<211> LENGTH: 18
<212> TYPE: DNA
<213> ORGANISM: Homo sapiens

<400> SEQUENCE: 4
tcatcatagg aaacacca                                                   18

<210> SEQ ID NO 5
<211> LENGTH: 20
<212> TYPE: DNA
<213> ORGANISM: Homo sapiens

<400> SEQUENCE: 5
caccaggctc tacagtaatg                                                 20

<210> SEQ ID NO 6
<211> LENGTH: 19
<212> TYPE: DNA
<213> ORGANISM: Homo sapiens

<400> SEQUENCE: 6
tgagaggcac ccttcacag                                                  19

<210> SEQ ID NO 7
<211> LENGTH: 19
<212> TYPE: DNA
<213> ORGANISM: Homo sapiens

<400> SEQUENCE: 7
gctcaactac gaactccct                                                  19

<210> SEQ ID NO 8
<211> LENGTH: 19
<212> TYPE: DNA
<213> ORGANISM: Homo sapiens

<400> SEQUENCE: 8
tgagaggcac ccttcacag                                                  19
```

```
<210> SEQ ID NO 9
<211> LENGTH: 21
<212> TYPE: DNA
<213> ORGANISM: Homo sapiens

<400> SEQUENCE: 9
aggaaatagt tggtggcatt c                                              21

<210> SEQ ID NO 10
<211> LENGTH: 14
<212> TYPE: DNA
<213> ORGANISM: Homo sapiens

<400> SEQUENCE: 10
tgcacctgac tcct                                                      14

<210> SEQ ID NO 11
<211> LENGTH: 17
<212> TYPE: DNA
<213> ORGANISM: Homo sapiens

<400> SEQUENCE: 11
cctgtcttgt aaccttg                                                   17

<210> SEQ ID NO 12
<211> LENGTH: 21
<212> TYPE: DNA
<213> ORGANISM: Homo sapiens

<400> SEQUENCE: 12
agaatataca cttctgctta g                                              21

<210> SEQ ID NO 13
<211> LENGTH: 33
<212> TYPE: DNA
<213> ORGANISM: artificial sequence
<220> FEATURE:
<223> OTHER INFORMATION: hybrid sequence - residues 1-15: a
      target-independent tail; residues 15-33 homologous to sequences
      from the CFTR gene (homo sapiens)

<400> SEQUENCE: 13
gctgcacgct gaggttcatc ataggaaaca cca                                 33

<210> SEQ ID NO 14
<211> LENGTH: 17
<212> TYPE: DNA
<213> ORGANISM: artificial sequence
<220> FEATURE:
<223> OTHER INFORMATION: synthetic indicator primer
<220> FEATURE:
<221> NAME/KEY: misc_feature
<222> LOCATION: (1)..(1)
<223> OTHER INFORMATION: fluorescent label
<220> FEATURE:
<221> NAME/KEY: misc_feature
<222> LOCATION: (1)..(1)

<400> SEQUENCE: 14
gggctgcacg ctgaggt                                                   17

<210> SEQ ID NO 15
<211> LENGTH: 17
<212> TYPE: DNA
<213> ORGANISM: Homo sapiens
```

```
<400> SEQUENCE: 15
gcgcggacat ggaggac                                                        17

<210> SEQ ID NO 16
<211> LENGTH: 32
<212> TYPE: DNA
<213> ORGANISM: artificial sequence
<220> FEATURE:
<223> OTHER INFORMATION: hybrid sequence - residues 1-15: a
      target-independent tail; residues 15-32 homologous to sequences
      from the apolipoprotein E gene (homo sapiens)

<400> SEQUENCE: 16
cgacgtggca gacgaccggc ctggtacact gc                                       32

<210> SEQ ID NO 17
<211> LENGTH: 17
<212> TYPE: DNA
<213> ORGANISM: artificial sequence
<220> FEATURE:
<223> OTHER INFORMATION: synthetic indicator primer
<220> FEATURE:
<221> NAME/KEY: misc_feature
<222> LOCATION: (1)..(1)
<223> OTHER INFORMATION: fluorescent label

<400> SEQUENCE: 17
cccgacgtgg cagacga                                                        17

<210> SEQ ID NO 18
<211> LENGTH: 17
<212> TYPE: DNA
<213> ORGANISM: Homo sapiens
<220> FEATURE:
<221> NAME/KEY: misc_feature
<222> LOCATION: (1)..(1)
<223> OTHER INFORMATION: fluorescent label

<400> SEQUENCE: 18
gcgcggacat ggaggac                                                        17

<210> SEQ ID NO 19
<211> LENGTH: 17
<212> TYPE: DNA
<213> ORGANISM: Homo sapiens
<220> FEATURE:
<221> NAME/KEY: misc_feature
<222> LOCATION: (1)..(1)
<223> OTHER INFORMATION: fluorescent label

<400> SEQUENCE: 19
ccggcctggt acactgc                                                        17

<210> SEQ ID NO 20
<211> LENGTH: 23
<212> TYPE: DNA
<213> ORGANISM: Homo sapiens
<220> FEATURE:
<221> NAME/KEY: misc_feature
<222> LOCATION: (1)..(6)
<223> OTHER INFORMATION: GC clamp selected from 6 to 60 residues in
      length

<400> SEQUENCE: 20
gcgcgcgcgc ggacatggag gac                                                 23
```

```
<210> SEQ ID NO 21
<211> LENGTH: 17
<212> TYPE: DNA
<213> ORGANISM: Homo sapiens
<220> FEATURE:
<221> NAME/KEY: misc_feature
<222> LOCATION: (1)..(1)
<223> OTHER INFORMATION: fluorescent label

<400> SEQUENCE: 21
ccggcctggt acactgc                                                    17
```